(12) United States Patent
Irache Garreta et al.

(10) Patent No.: US 8,895,067 B2
(45) Date of Patent: Nov. 25, 2014

(54) IMMUNE RESPONSE STIMULATING COMPOSITION COMPRISING NANOPARTICLES BASED ON A METHYL VINYL ETHER-MALEIC ACID COPOLYMER

(75) Inventors: Juan Manuel Irache Garreta, Pamplona (ES); Carlos Gamazo De La Rasilla, Obanos (ES); Maria Luisa Sanz Larruga, Pamplona (ES); Marta Ferrer Puga, Pamplona (ES); Beatriz San Román Aberasturi, Alsasua (ES); Hesham H. A. Salman, Pamplona (ES); Sara Gómez Martinez, Logroño (ES); Javier Ochoa Repàraz, Olaz de Egüés (ES)

(73) Assignee: Universidad de Navarra, Pamplona (Navarra) (ES)

( * ) Notice: Subject to any disclaimer, the term of this patent is extended or adjusted under 35 U.S.C. 154(b) by 1777 days.

(21) Appl. No.: 11/568,455

(22) PCT Filed: Apr. 28, 2005

(86) PCT No.: PCT/ES2005/000225
§ 371 (c)(1),
(2), (4) Date: Dec. 4, 2006

(87) PCT Pub. No.: WO2005/105056
PCT Pub. Date: Nov. 10, 2005

(65) Prior Publication Data
US 2007/0224225 A1 Sep. 27, 2007

(30) Foreign Application Priority Data
Apr. 29, 2004 (ES) .................................. 200401023

(51) Int. Cl.
*A61K 9/14* (2006.01)
*A61K 36/00* (2006.01)
*A61K 36/06* (2006.01)
*A61K 39/112* (2006.01)
*A61K 39/39* (2006.01)
*B82Y 5/00* (2011.01)
*A61K 51/12* (2006.01)
*A61K 39/00* (2006.01)

(52) U.S. Cl.
CPC . *A61K 36/00* (2013.01); *A61K 9/14* (2013.01); *A61K 51/1244* (2013.01); *A61K 2201/103* (2013.01); *A61K 36/06* (2013.01); *A61K 39/0275* (2013.01); *A61K 39/39* (2013.01); *A61K 2039/55555* (2013.01); *A61K 2039/55572* (2013.01); *A61K 2039/55594* (2013.01); *B82Y 5/00* (2013.01); *Y10S 977/773* (2013.01)
USPC ............ 424/489; 424/490; 424/497; 977/773

(58) Field of Classification Search
USPC ........................................................ 424/489
See application file for complete search history.

(56) References Cited

U.S. PATENT DOCUMENTS

| | | | |
|---|---|---|---|
| 4,582,865 A | 4/1986 | Balazs et al. | |
| 4,904,479 A | 2/1990 | Illum | |
| 5,133,908 A * | 7/1992 | Stainmesse et al. | 264/4.1 |
| 5,578,325 A | 11/1996 | Domb et al. | |
| 5,962,566 A | 10/1999 | Grandfils et al. | |
| 6,066,340 A | 5/2000 | Callegaro et al. | |
| 6,132,750 A | 10/2000 | Perrier et al. | |
| 6,322,817 B1 | 11/2001 | Maitra et al. | |
| 6,383,478 B1 | 5/2002 | Prokop et al. | |
| 6,465,425 B1 | 10/2002 | Tracy et al. | |
| 6,660,810 B1 | 12/2003 | Ferruti et al. | |
| 2001/0053359 A1 | 12/2001 | Watts et al. | |
| 2002/0009466 A1 | 1/2002 | Brayden | |
| 2002/0009493 A1 | 1/2002 | Schwendeman et al. | |
| 2002/0061315 A1* | 5/2002 | Kundig et al. | 424/275.1 |
| 2002/0197328 A1 | 12/2002 | Kim et al. | |
| 2003/0026844 A1 | 2/2003 | Lee et al. | |
| 2003/0059465 A1 | 3/2003 | Unger et al. | |
| 2003/0147965 A1* | 8/2003 | Bassett et al. | 424/490 |
| 2005/0079222 A1* | 4/2005 | Arbos Vila et al. | 424/490 |
| 2006/0134785 A1 | 6/2006 | Fernandez et al. | |

FOREIGN PATENT DOCUMENTS

| | | |
|---|---|---|
| EP | 0275796 | 7/1988 |
| EP | 0544259 A1 | 6/1993 |
| ES | 2098188 B1 | 4/1997 |
| ES | 2098189 B1 | 4/1997 |
| ES | 2114502 B1 | 5/1998 |
| WO | 8903207 A1 | 4/1989 |

(Continued)

OTHER PUBLICATIONS

Benedetti, L.M., et al., "Microspheres of hyaluronic acid esters Fabrication methods and in vitro hydrocortisone release", "J. Control. Rel.", Jul. 1990, pp. 33-41, vol. 13, No. 1.
Blanco, M.D., et al., "Development and characterization or protein-loaded poly(lactide-co-glycolide) nanospheres", "Eur. J. Pharm. Biopharm.", Jun. 1997, pp. 287-294, vol. 43, No. 3.
Blanco, Dolores, et al., "Protein encapsulation and release from poly(lactide-co-glycolide) microspheres: effect of the protein and polymer properties of the co-encapusulation of surfactants", "Eur. J. Pharm Biopharm.", May 1998, pp. 285-294, vol. 45, No. 3.
Hawley, Ann E., et al., "Lymph node localisation of biodegradable nanospheres surface modified with poloxamer and poloxamine block co-polymers", "FEBS Letter", Jan. 6, 1997, pp. 319-323, vol. 400, No. 3.

(Continued)

*Primary Examiner* — James Rogers
(74) *Attorney, Agent, or Firm* — Hultquist, PLLC; Steven J. Hultquist; Mary B. Grant

(57) ABSTRACT

The composition for stimulating an immune response in a subject comprises methyl vinyl ether and maleic anhydride copolymer-based nanoparticles. Said nanoparticles may further contain an allergen or an antigen and/or an immunostimulating agent, which may be contained inside said nanoparticles and/or at least partially coating the surface of said nanoparticles, and optionally a cross-linking agent. The immune response stimulating composition is useful as an adjuvant in immunotherapy and vaccines.

12 Claims, 12 Drawing Sheets

(56) References Cited

FOREIGN PATENT DOCUMENTS

| WO | 9009401 A1 | 8/1990 |
|---|---|---|
| WO | 9606622 A1 | 3/1996 |
| WO | 0620698 A2 | 7/1996 |
| WO | 9704747 A1 | 2/1997 |
| WO | 9947130 A1 | 9/1999 |
| WO | 0012125 A1 | 3/2000 |
| WO | 0101964 A2 | 1/2001 |
| WO | 9918934 A12 | 1/2001 |
| WO | 0128602 A1 | 4/2001 |
| WO | 0182724 A2 | 11/2001 |
| WO | 0230990 A1 | 4/2002 |
| WO | WO 02069938 A1 * | 9/2002 |
| WO | 2004009060 A1 | 1/2004 |
| WO | WO 2005/014648 | 11/2005 |
| WO | WO 2005/105056 | 11/2005 |

OTHER PUBLICATIONS

Kabanov, Alexander V., et al., "Pluronic block copolymers as modulators of drug efflux transporter activity in the blood-brain barrier", "Adv. Drug. Deliv. Rev.", Jan. 21, 2003, pp. 151-164, vol. 55, No. 1.
Lemieux, P., et al., "A combination of poloxamers increases gene expression of plasmid DNA in skeletal muscle", "Gene Therapy", Jun. 2000, pp. 986-991, vol. 7, No. 11.
Lim, S.T., et al., "Preparation and evaluation of the in vitro drug release properties and mucodhesion of novel microspheres of hyaluronic acid and chitosan, J. Control. Rel.", May 15, 2000, pp. 281-292, vol. 86, No. 2-3.
Lim, S.T., et al., "In vivo evaluation of novel hyaluronan/ohitosan microparticulate delivery systems for the nasal delivery of gentamicin I", "Int. J. Pharm.", Jan. 1, 2002, pp. 73-82, vol. 231, No. 1.
Lourenco, Christina, et al., "Steric stabilization of nanoparticles: Size and surface properties", "Int. J. Pharm.", Jul. 12, 1996, pp. 1-12, vol. 138, No. 1.
Moghimi, S.M., et al., "Surface engineered nanospheres with enhanced drainage into lymphatics and uptake by macrophages of the regional lymph nodes.", "FEBS Letters", May 9, 1994, pp. 25-30, vol. 344, No. 1.
Sanchez, Alejandro, et al., "Development of biodegradable microspheres and nanospheres for the controlled release of cyclosphorin A", "Int. J. Pharm.", Oct. 15, 1993, pp. 263-273, vol. 99, No. 2-3.
Sanchez, Alejandro, et al., "Biodegradable mciro- and nanoparticles as long-term delivery vehicles for interferon-alpha", "Eur. J. of Pharm. Sci.", Mar. 2003, pp. 221-229, vol. 18, No. 3-4.
Tobio, Maria, et al., "A Novel System Based on a Poloxamer/PLGA Blend as a Tetanus Toxoid Delivery Vehicles", "Pharm. Res.", May 1999, pp. 682-688, vol. 16, No. 5.
Yoncheva, K. et al., "Pegylated nanoparticles based on poly(methyvinyl ether-co-maleic anhydrude): preparation and evaluation of their bioadhesive properties", *Eur. J. Pharm. Sci .*, 24:5 (2005), pp. 411-419.
Chiellini, E., et al., "Design of polymeric systems for targeted administration of peptide and protein drugs", *Polymer Preprints*, 39:2(1998), pp. 182-183.
Arbos, P., et al., "Gantrez® AN as a new polymer for the preparation of ligand-nanoparticle conjugates", *Journal of Controlled Release*, 83:3 (2002), pp. 321-330.
Arbos, P. et al., "Quantification of the bioadhesive properties of protein-coated PVM/MA nanoparticles", *International Journal of Pharmaceutics*, 242:1-2 (2002), pp. 129-136.
Gomez, S. et al., "Gantrez® AN nanoparticles as an adjuvant for oral immunotherapy with allergens", "Vaccine", 2007, pp. 5263-5271, vol. 25.
Gomez, S. et al. , "A novel nanoparticulate adjuvant for immunotherapy with *Lolium perenne*", "Journal of Immunological Methods", 2009, pp. 1-8, vol. 348.
Ochoa, J. et al., "Protective immunity of biodegradable nanoparticle-based vaccine against an experimental challenge with *Salmonella* Enteritis in Mice", "Vaccine", 2007, pp. 4410-4419, vol. 25.

Tamayo, I. et al., "Poly(Anhydride) Nanoparticles Act as Active Th1 Adjuvants through Toll-Like Receptor Exploitation", Sep. 2010, pp. 1356-1362, vol. 17, No. 9.
Lai, S. et al. , "Rapid transport of large polymeric nanoparticles in fresh undiluted human mucus", PNAS, Jan. 30, 2007, pp. 1482-1487, vol. 104, No. 5.
Wang, Y. et al. , "Addressing the PEG Mucoadhesivity Paradox to Engineer Nanoparticles that Slip through the Human Mucus Barrier", "Angew Chem Int Ed Engl.", 2008, pp. 9726-9729, vol. 47, No. 50.
Yoncheva, K. et al. , "Evaluation of bioadhesive potential and intestinal transport of pegylated poly(anhydride) nanoparticles", Int'l Journal of Pharmaceutics, 2007, pp. 156-165, vol. 334.
Conway, M.A., et al., "Protection against *Bordetella pertussis* infection following parenteral or oral immunization with antigens entrapped . . . ", "Vaccine", 2001, pp. 1940-1950, vol. 19.
Cui, Z., et al., "Strong T cell type-1 immune responses to HIV-I Tat (1-72) protein-coated nanoparticles", "Vaccine", 2004, pp. 2631-2640, vol. 22.
Debin, A., et al., "Intranasal immunization with recombinant antigens associated with new cationic particles induces strong mucosal . . . ", "Vaccine", 2002, pp. 2752-2763, vol. 20.
Kim, S.Y., et al., "Oral Immunization with *Helicobacter* pylon-Loaded Poly(D,L-Lactide-Co-Glycolide) Nanoparticles", "*Helicobacter*", 1999, p. 1999 vol. 4, No. 1.
Scholl, I., et al., "Allergen-loaded biodegradable poly(D,L-lactic-co-glycolic) acid nanoparticles down-regulate an ongoing Th2 response . . . ", "Clin Exp Allergy", 2004, pp. 315-321, vol. 34.
Challacombe, S., et al., "Enhanced secretory IgA and systemic IgG antibody responses after oral immunization with biodegradable microparticles containing antigen", "Immunology", May 1992, pp. 164-168, vol. 76.
Couvreur, P., et al., "Nano- and microparticles for the delivery of polypeptides and proteins", "Advanced Drug Delivery Reviews", May-Jun. 1993, pp. 141-162, vol. 10.
Eldridge, J., et al., "Controlled Vaccine Release in the Gut-Associated Lymphoid Tissues. I. Orally Administered Biodegradable Microspheres Target the Peyer's Patches", "Journal of Controlled Release", Jan. 1990, pp. 205-214, vol. 11.
Finne, U., et al., "Mechanisms of timolol release from monoisopropyl PVM-MA matrices with and without a basic salt", "International Journal of Pharmaceutics", Jan. 1, 1992, pp. 237241, vol. 78.
Jones, D., et al., "Poly(DL-lactide-co-glycolide)-encapsulated plasmid DNA elicits systemic and mucosal antibody responses to encoded protein after oral administration", "Vaccine", Jun. 1997, pp. 814-817, vol. 15, No. 8.
Moore, A., et al., "Immunization with a soluble recombinant HIV protein entrapped in biodegradable microparticles induces HIV-specific CD8+ cytotoxic T lymphocytes and CD4+ Th1 cells", "Vaccine", Dec. 1995, pp. 1741-1749, vol. 13, No. 18.
Murillo, M., et al., "A *Brucella ovis* antigenic complex bearing poly-epsilon-caprolactone microparticles confer protection against experimental brucellosis in mice", "Vaccine", Jul. 20, 2001, pp. 4099-4106, vol. 19, No. 30.
Nixon, D., et al., "Synthetic peptides entrapped in microparticles can elicit cytotoxic T cell activity", "Vaccine", Nov. 1996, pp. 1523-1530, vol. 14, No. 16.
Singh, M., et al, "Recent advances in veterinary vaccine adjuvants", "Int J Parasitol.", May 2003, pp. 469-478, vol. 33, No. 5-6.
Allaoui-Attarki, K., et al., "Protective Immunity against *Salmonella typhimurium* Elicited in Mice by Oral Vaccination with Phosphorylcholine Encapsulated in Poly(DL-Lactide-Co-Glycolide) Microspheres", "Infection and Immunity", Mar. 1997, pp. 853-857, vol. 65, No. 3.
Cahill, E., et al., "Immune responses and protection against *Bordetella pertussis* infection after intranasal immunization of mice with filamentous haemagglutinin in solution or incorporated in biodegradable microparticles", "Vaccine", Apr. 1995, pp. 455-462, vol. 13, No. 5.
Maloy, K., et al., "Induction of mucosal and systemic immune responses by immunization with ovalbumin entrapped in poly(lactide-co-glycolide) microparticles", "Immunology", Apr. 1994, pp. 661-667, vol. 81, No. 4.

(56) References Cited

OTHER PUBLICATIONS

Putney, S., et al., "Improving protein therapeutics with sustained-release formulations", "Nature Biotechnology", Feb. 1998, pp. 153-157, vol. 16, No. 2.

Shahin, R., et al., "Adjuvanticity and Protective Immunity Elicited by *Bordetella pertussis* Antigens Encapsulated in Poly(DL-Lactide-Co-Glycolide) Microspheres", "Infection and Immunity", Apr. 1995, pp. 1195-1200, vol. 63, No. 4.

Whittum-Hudson, J., et al., "Oral immunization with an anti-idiotypic antibody to the exoglycolipid antigen protects against experimental *Chlamydia trachomatis* infection", "Nature Medicine", Oct. 1996, pp. 1116-1121, vol. 2, No. 10.

\* cited by examiner

IMMUNE RESPONSE STIMULATING COMPOSITION COMPRISING NANOPARTICLES BASED ON A METHYL VINYL ETHER-MALEIC ACID COPOLYMER

CROSS-REFERENCE TO RELATED APPLICATIONS

This application is filed under the provisions of 35 U.S.C. §371 and claims the benefit of priority of International Patent Application No. PCT/ES2005/000225, filed Apr. 28, 2005, which in turn claims priority of Spanish Patent Application No. P 200401023, filed Apr. 29, 2004. The disclosures of all said applications are hereby incorporated herein by reference in their respective entireties.

FIELD OF THE INVENTION

The invention relates to the use of methyl vinyl ether-maleic anhydride copolymer-based nanoparticles, optionally containing an allergen or an antigen and/or an immunostimulating agent, as adjuvants in immunotherapy and vaccines. The invention also relates to immune response stimulating compositions comprising said nanoparticles.

BACKGROUND OF THE INVENTION

As it is known, there are highly immunogenic antigens that are able to induce protective immune responses in a subject, whereas there are other antigens that do not induce said protective response or which induce a very weak immune response. Generally, the immune response of the host to a weakly immunogenic antigen may be stimulated by means of the joint administration of an adjuvant.

Adjuvants

An adjuvant is any substance that increases the immune response to an antigen with which it is mixed. Adjuvants mainly act by means of three mechanisms: i) forming an antigen or allergen deposit at the vaccine application site from which the biologically active product will be released during a variable period of time; ii) delivering the antigen or allergen to the antigen-presenting cells; and iii) inducing interleukin secretion.

Some classic examples of adjuvants are: aluminum salts (Alhydrogel) and catecholamines, (which enhance a Th2 response), and the lipopolysaccharide of gram-negative bacteria and certain CpG sequences (which enhance the Th1 response). On the other hand, numerous studies demonstrate that certain non-biological vectors such as microparticles (spherical particles of polymeric nature coating a substance) or liposomes (spherical vesicles with an aqueous central cavity coated by a variable number of bimolecular phospholipid and cholesterol films) can also act as adjuvants [Eldridge et al., *Infect Immun*, 59 (1991) 2978-2986; O'Hagan et al., *Vaccine*, 18 (2000) 1793-1801; Murillo et al., *Vaccine*, 30 (2001) 4099-4106].

Another type of non-biological vectors which can be considered for their use as adjuvants are the solid particle colloidal systems with less than a micrometer in size, also called nanoparticles, which are subdivided into matrix nanospheres and vesicular nanocapsules [Orecchioni and Irache, *Formes pharmaceutiques pour application locale*. Lavoisier Tech and Doc., Paris, (1996) 441-457]. Nanocapsules are vesicular systems formed by an inner cavity that is surrounded by a polymer membrane or wall. Nanospheres are matrix forms, formed by a three-dimensional polymer network. In both cases, the molecules of the biologically active substance can be dissolved, trapped or bound in the macromolecular structure (in the nanospheres) or encapsulated by the polymer membrane (in the nanocapsules), and it can even be adsorbed to the nanoparticle surface.

The distribution of nanoparticles in the organism is, in general, dependent on its physicochemical characteristics (mainly size and surface properties) determining its interaction with the biological medium. Therefore they are pharmaceutical forms that are particularly interesting as immunotherapy or vaccine adjuvants for the administration of antigens and/or allergens.

In general, the most important potentials provided by these vectors of non-biological origin are as follows [Couvreur & Puisieux. *Adv. Drug Del. Rev.*, 10 (1993) 141-162]: (i) they protect the encapsulated material from chemical, enzymatic or immunological inactivation at the administration and action site; (ii) they improve the transport of the biologically active molecule to hard-to-reach locations and its penetration in the cell; (iii) they prolong the drug residence time in the organism and control its release; (iv) they increase action specificity by selective, effective and regular concentration of the encapsulated material in the cellular and/or molecular target; and (v) they increase the stability of the material that they incorporated during manufacture, transport and storage of the medicinal product.

Use of Adjuvants in Vaccination

The use of particulate adjuvants in the form of emulsions, microparticles, ISCOMS or liposomes has previously been evaluated by several investigation groups [review: Singh et al., *Int J Parasitology* 33 (2003) 469-478].

Antigen capture by "antigen-presenting cells" increases when these antigens are associated with polymeric particles or are included inside them. Biodegradable and biocompatible polyesters have been used in humans and animals for many years as controlled antigen release systems [Okada et al., *J Pharm Sci*, 12 (1995) 1-99; Putney et al., *Nat Biotechnol*, 16 (1998) 153-157]. Unlike aluminum adjuvants, microparticles are effective in inducing cellular and cytotoxic immune responses in mice [Nixon et al., *Vaccine* 14 (1996) 1523-1530; Maloy et al., *Immunology* 81 (1994) 661-667; Moore et al., *Vaccine* 13 (1995) 1741-1749]. Oral immunization with microparticles in mice induces potent immune responses at the mucosal and systemic levels compared to encapsulated antigens [Chalacombe et al., *Immunology* 176 (1992) 164-168; Eldridge et al., *J Control Rel* 11 (1990) 205-214; O'Hagan et al., *Novel Delivery Systems for Oral Vaccines* (1994) 175-205]. This ability is the result of its internalization by specialized cells of the mucosa-associated lymphoid tissue [O'Hagan, *J Anat*, 189 (1996) 477-482]. Mucosal immunization with different particulate systems has demonstrated its effectiveness against different pathogens, such as *Bordetella pertussis* [Chaill et al., *Vaccine* 13 (1995) 455-462; Jones et al., *Vaccine* 15 (1997) 814-817; Shahin et al., *Infect Immun*, 63 (1995) 1195-1200; Conway et al., *Vaccine* 19 (2001) 1940-1950], *Chlamydia trachomatis* [Whittum-Hudson et al., *Nat Med* 2 (1996) 1116-1121], *Salmonella Typhimurium* [Allaoui-Attarki et al., *Infect Immun* 65 (1997) 853-857] and *Brucella* [Murillo et al., *Vaccine*, 19 (2001) 4099-4106].

Use of Adjuvants in Immunotherapy

Allergic diseases are an emerging pathology caused by an adverse immune response (hypersensitivity reaction) to intrinsically innocuous macromolecules, called allergens. This hypersensitivity affects about 30% of the population worldwide, mainly in industrialized countries. It is the cause of diseases such as allergic rhinitis, extrinsic asthma, food allergies and allergies to drugs and insects [Settipane et al., *Allergy Proc*, (1994) 21-25].

In Spain, the prevalence of this type of diseases in the population of 4 to 17 years of age is 13.3%; among them, 6.4% appear as bronchial asthma, the death rate due to asthma in Spain being 1.5/100,000 inhabitants.

The mechanistic theory of the cause of allergic diseases argues that they occur due to an altered balance between the two fundamental types of responses that may be generated after activating the T helper cells: Th1 and Th2. Cytokines present in the medium outside the cell affect in a determining manner the differentiation of immature T cells (Th0), such that the presence of interleukin 12 (IL-12), interferon gamma (IFN-$\gamma$), interleukin 18 (IL-18) and interferon alpha (IFN-$\alpha$), induce differentiation towards Th1, which will mainly be characterized by the production of large quantities of IFN-$\gamma$, and, to a lesser degree, of interleukin 2 (IL-2) and interferon beta (IFN-$\beta$). The subsequent stimulation of B cells in this type of response will give rise to the production of $IgG_{2a}$, $IgG_{2b}$ and $IgG_3$. On the other hand, if the Th0 cell is in an environment in which interleukin 4 (IL-4) and prostaglandin E2 (PGE2) are predominant, differentiation towards Th2 will be induced, being characterized by the synthesis of large quantities of IL-4, interleukin 5 (IL-5) and interleukin 13 (IL-13), and by the synthesis of $IgG_1$ and IgE, a biotype directly involved in the triggering process [Hannah et al., *Ann Rev Immunol*, 21 (2003) 579-628].

The importance of the predominance of a Th2, allergenic-specific type response in allergic diseases has been corroborated by a large number of studies [Romagnani, *Ann Rev Immunol*, 12 (1994) 227; Bousquet et al., *Allergy*, 53 (1998) 1-42; Majori et al., *Clin Exp Allergy*, 30 (2000) 341-347]. It has been demonstrated both in animal models and in man, that cells with a Th2 phenotype are the only cells able to directly recognize allergenic peptides and participate in the production of IgE by B cells, mastocyte activation and production, maturation and activation of eosinophils [Cohn et al., *Pharmacology and Therapeutics*, 88 (2000) 187-196].

Therefore, the functional predominance of Th2 over Th1 cells would lead to the allergic response, whereas the functional predominance of Th1 over Th2 cells would inhibit it [Martin et al., *Alergol Immunol Clin*, 17 (2002) 104-110].

Other studies claim that inhibition of a Th2 response with Th1 predominance could lead to the development of autoimmune diseases, so it would be more correct to enhance an immune regulation of the Th1/Th2 balance by increasing the population of regulatory T cells (Tr) and IL-10, and T cell growth factor $\beta$ (TGF-$\beta$). This would lead to the synthesis of $IgG_4$ and IgA antibodies (not inflammatory response mediators), and to the suppression of IgE production by B cells [Akdis et al., *Immunology*, 103 (2001) 131-136; Akdis et al., *J Clin Invest*, 102 (1998) 98-106; Blaser et al., *Int Arch Allergy Immunol*, 117 (1998) 1-10]. Recent studies reaffirm the importance of IL-10 in Th2 cell inactivation (Grunig et al., *J Exp Med*, 185 (1997) 1089-1099; Adachi et al., *Int Arch Allergy Immunol*, 118 (1999) 391-394], and it has even been found that in vivo administration of IL-10 has beneficial consequences in allergic animals [Zuany-Amorim et al., *J Clin Invest*, 95 (1995) 2644-2651; Stampfli et al., *Am J Respir Cell Mol Biol*, 21 (1999) 586-596; Hall et al., *Vaccine*, 21 (2003) 549-561]. This allows supposing that IL-10 plays an important regulatory role in Th2 cell hyperreactivity characteristic in allergic patients.

IL-10 can have important physiopathological implications for counteracting inflammatory diseases (Crohn's disease, rheumatoid arthritis, psoriasis, etc.), certain viral infections (hepatitis C, human immunodeficiency virus (HIV)-induced infections, etc.), or even inhibiting organ transplant side effects. Therefore, the direct application of IL-10, or else the use of adjuvants stimulating the production of IL-10, could have a huge impact on the treatment of these diseases [Asadullah et al., *Pharmacol Rev*, 55, (2003) 241-269]. It is currently being studied as a possible treatment for autoimmune diseases such as rheumatoid arthritis [Feldman et al., *Annu Rev Immunol* (1996) 397-440; Katsikis et al., *J Exp Med* (1994) 1517-1527; Chomarat et al., *J Immunol* (1995) 1432-1439]. The antiinflammatory and regulatory role of the cytokine therefore makes it essential in both Th1 (autoimmune diseases) and Th2 (allergy) excessive responses.

The treatment of allergic diseases may essentially be approached in three different manners: (i) avoiding all contact with the allergen; (ii) using antihistaminic drugs, and (iii) by means of immunotherapy. Bearing in mind that the first two measures are occasionally not applicable, immunotherapy would be the most suitable control method.

Specific immunotherapy with allergens has been defined as the repeated administration of allergens to patients with IgE-mediated health disorders for the purpose of providing protection against allergic symptoms and inflammatory reactions associated with the natural exposure to these allergens [Jutel, M., *J Immunol*, 154 (1995) 4178-4194].

This treatment alternative is aimed at enhancing a functional predominance of the Th1 response with respect to the Th2 response, which will inhibit the allergic symptomatology. This modulation towards Th1 is also applicable in other processes such as control by means of vaccination against bacterial intracellular parasites (such as *Brucella* and *Salmonella*).

Although the use of different non-biological vectors, for example nanoparticles, as adjuvants in immunotherapy or in vaccines for the administration of antigens and/or allergens has been described, there is still a need to provide alternative adjuvants to those currently existing for the purpose of increasing the arsenal of possibilities for manufacturing vaccines and compositions for immunotherapy. Advantageously, said adjuvants must be useful for their use in immunization or immunotherapy by oral administration without the need to use very high allergen and antigen doses. As is known, despite its potential advantages, oral immunization for therapeutic or prophylactic purposes must confront several obstacles since the dose of the immunogenic or allergenic active ingredient required for a beneficial clinical effect is extremely high due to an immunogen potency loss. Therefore, generally due to the little stability of the allergen or antigen in the gastrointestinal tract (pH conditions and presence of hydrolytic enzymes), doses must always be much higher (up to 200 times higher) than those normally used subcutaneously [Taudorf et al., *J Allergy Clin Immunol* (1987) 153-161; Creticos et al., *J Allergy Clin Immunol* (1990) 165]. Furthermore, the gastrointestinal mucosa acts as a rather impermeable barrier against the absorption of these macromolecules.

Surprisingly, it has now been found that methyl vinyl ether-maleic anhydride copolymer-based nanoparticles, optionally containing an allergen or antigen and/or an immunostimulating agent, have the ability to stimulate or enhance immune response when they are administered to a subject, which allows their use in immunotherapy and vaccines. Said nanoparticles are stable in oral administration, have good bioadhesive characteristics, and can therefore be used in immunization or immunotherapy through different administration routes, including the oral route, without needing to use such high allergen or antigen doses as those mentioned in the state of the art. Furthermore, said nanoparticles are low toxic, they are biodegradable and easy to produce.

Methyl Vinyl Ether-Maleic Anhydride Copolymer Nanoparticles

Patent application WO 02/069938, belonging to the same applicant, discloses methyl vinyl ether-maleic anhydride (PVM/MA) copolymer nanoparticles, a process for obtaining them and their use as drug carriers. Said PVM/MA copolymer structurally consists of two differentiated functional groups having different solubility characteristics: a hydrophobic ester group and an anhydrous group. The carboxylic group is a solubilizing agent, since it tends to dissolve the polymer when it is ionized, and the ester group is hydrophobic, as it delays penetration of water into the polymer [Heller et al., *J Appl Polym Sci*, 22 (1978) 1991-2009]. Synthetic PVM/MA copolymers have very different applications. Gantrez® AN is widely used as a thickener and flocculating agent, dental adhesive, excipient in oral tablets, excipient in transdermal patches, etc. On the other hand, the use of these copolymers for controlled release of drugs has been disclosed [Heller et al., *J Appl Polym Sci*, 22 (1978) 1991-2009] and, in matrix forms, for topical release of drugs in the eye [Finne et al., *J Pharm Sci*, 80 (1991) 670-673; Finne et al., *Int J Pharm*, 78 (1992) 237-241].

PVM/MA-based nanoparticles have bioadhesive characteristics [Arbós et al., *Int J Pharm*, (2002) 129-136] so that when they are administered orally, they may interact with Peyer's patches, which contain 20% of all the lymphocytes of the organism, and trigger an amplified immune response with regard to that of antigens and/or allergens administered in aqueous solution.

PVM/MA-based nanoparticles are colloidal systems that are able to retain biologically active substances by means of: (i) solution or entrapping inside the macromolecular structure or matrix, (ii) covalent bond of the drug with the copolymer anhydride groups and (iii) adsorption processes mediated by weak bonds. The extreme reactivity of the PVM/MA copolymer, due to cyclic anhydride groups, also contributes to its ability to entrap molecules, drugs or other substances. Patent application WO 02/069938 discloses the use of said PVM/MA copolymer nanoparticles as carriers for drugs, specifically 5-fluouridine, ganciclovir and antisense oligonucleotide ISIS 2922.

SUMMARY OF THE INVENTION

The object of the present invention is to provide an immune response stimulating composition in a subject useful as an adjuvant in immunotherapy and vaccines, stable when orally administered, that has good bioadhesive characteristics for its interaction with mucosae, able to optionally carry an allergen or antigen and/or an immunostimulating agent and to release said products in a controlled manner, and therefore useful in immunization or immunotherapy by different administration routes, including orally.

Surprisingly, it has now been found that methyl vinyl ether-maleic anhydride copolymer-based nanoparticles, optionally containing an allergen or antigen and/or an immunostimulating agent, have the ability to stimulate or enhance immune response when they are administered to a subject, which allows their use in immunotherapy and vaccines. It has particularly been found that said nanoparticles are easy to produce, have good bioadhesive characteristics, are low toxic and are biodegradable (i.e. they dissolve or degrade in a period of time that is acceptable for the desired application, in this case in vivo therapy, once they are exposed to a physiological solution of pH 6-9 and a temperature comprised between 25° C. and 40° C.).

Therefore, in one aspect the invention relates to an immune response stimulating composition comprising methyl vinyl ether-maleic anhydride copolymer-based nanoparticles. Said nanoparticles may further contain an allergen or an antigen and/or an immunostimulating agent, which may be contained inside said nanoparticles and/or at least partially coating the surface of said nanoparticles. If so desired, said metabolic pathways may also contain a cross-linking agent. Said composition may optionally be in lyophilized form.

In another aspect, the invention relates to a vaccine or immunotherapy composition comprising said immune response stimulating composition. In a particular embodiment, said immunotherapy vaccine or composition is a suitable formulation for oral administration, whereas in another particular embodiment, said immunotherapy vaccine or composition is a suitable formulation for parenteral administration.

In another aspect, the invention relates to the use of said immune response stimulating composition in the manufacture of a vaccine or immunotherapy composition.

In another aspect, the invention relates to the use of said immune response stimulating composition in the manufacture of a pharmaceutical composition for the selective stimulation of immune response Th1, or in the manufacture of a pharmaceutical composition for the selective stimulation of immune response Th2, or in the manufacture of a pharmaceutical composition for the balanced stimulation of immune responses Th1 and Th2.

In another aspect, the invention relates to a process for producing an immune response stimulating composition comprising said PVM/MA-based nanoparticles and an allergen or an antigen and/or an immunostimulating agent comprising the addition of said allergen or antigen and/or immunostimulating agent to an organic solution comprising said PVM/MA copolymer before performing desolvation with a hydroalcoholic solution, or alternatively incubating said allergen or said antigen and/or with said immunostimulating agent with said PVM/MA nanoparticles. Said process may further comprise additional organic solvent elimination and/or purification steps as well as steps to stabilize the nanoparticles obtained by means of using cross-linking agents. Said process may optionally comprise an additional lyophilization step.

DETAILED DESCRIPTION OF THE INVENTION

Figure 1:
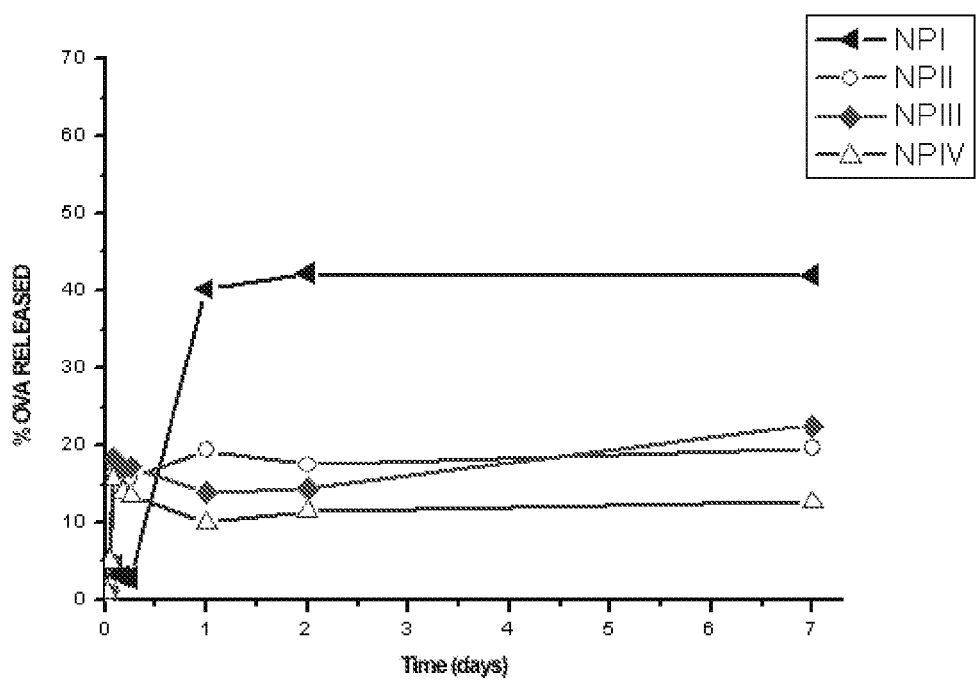
FIG. 1 shows a graph representing ovalbumin released (%) from the formulations NP-I, NP-II, NP-III and NP-IV over time (days).

Surprisingly, it has now been found that methyl vinyl ether-maleic anhydride copolymer-based nanoparticles optionally containing an allergen or antigen and/or an immunostimulating agent have the ability to stimulate or enhance immune response when administered to a subject, which allows their use in immunotherapy and vaccines.

The term "subject" as it is used herein, includes any animal having an immune system, preferably mammals, more preferably, human beings.

In one aspect, the invention relates to an immune response stimulating composition, hereinafter composition of the invention, comprising methyl vinyl ether and maleic anhydride copolymer nanoparticles. Said nanoparticles may further comprise an allergen or an antigen and/or an immunostimulating agent, which may be contained inside said nanoparticles and/or at least partially coating the surface of said nanoparticles. If so desired, said nanoparticles may also contain a cross-linking agent.

As it is used in this description, the term "nanoparticles" is used to designate solid particle-type colloidal systems with a size of less than 1.0 micrometer, preferably in the order of 10 to 900 nanometers (nm), and includes matrix nanospheres and vesicular nanocapsules. In a particular embodiment, said nanoparticles have a mean size that is equal to or less than 400 nm.

The nanoparticles present in the composition of the invention comprise a methyl vinyl ether-maleic anhydride copolymer, also called poly(methyl vinyl ether-co-maleic anhydride) or PVM/MA. Said PVM/MA copolymer is a known product that can be obtained by conventional methods, for example by means of polymerizing acetylene with maleic anhydride, or it can be obtained on the market. In this sense, the International Specialty Products (ISP) company produces PVM/MA copolymers having different molecular weights marketed under the trade name Gantrez® AN. In general, in order to put the present invention into practice, the molecular weight of said PVM/MA copolymer may vary within a very broad range, preferably between 100 and 2,400 KDa, more preferably between 200 and 2,000 KDa. In a variant of the invention, a PVM/MA copolymer with a molecular weight comprised between 180 and 250 kDa is preferred.

The use of said PVM/MA copolymer is very advantageous given that it is widely used in pharmaceutical technology due to its low toxicity (LD 50=8-9 g/kg orally) and its excellent biocompatibility. Furthermore, it is easy to obtain and can react with other hydrophilic substances due to its functional groups, without having to resort to the usual organic reagents (glutaraldehyde and carbodiimide derivatives) having important toxicity [Arbós et al., J. Controlled Rel., 83 (2002) 321-330]. The PVM/MA copolymer is insoluble in an aqueous medium, but the anhydride group present therein hydrolyzes, generating carboxylic groups. The solution is slow and depends on the conditions in which it is produced. Due to the availability of functional groups in PVM/MA, covalent bonding of molecules with nucleophilic groups, such as hydroxyls or amines, takes place by simple incubation in an aqueous medium. Said PVM/MA nanoparticles also have bioadhesive properties [Arbós et al., Int J Pharm, (2002) 129-136], so when administered orally they can interact with Peyer's patches, which contain 20% of all the lymphocytes of the organism, and trigger an amplified immune response with regard to that of antigens and/or allergens administered in aqueous solution.

In a particular embodiment, the composition of the invention comprises PVM/MA-based nanoparticles lacking an antigen or allergen and an immunostimulating agent. Said nanoparticles are called "empty" nanoparticles in this description and can be easily obtained by means of a process such as that disclosed in patent application WO 02/069938, the entire content of which is herein incorporated by reference. By way of illustration, said empty nanoparticles are easily prepared by desolvation with a hydroalcoholic phase of a solution of a PVM/MA copolymer in acetone. The formed nanoparticles can be left in a stable aqueous suspension or they can be lyophilized. A cross-linking agent can optionally be added. Virtually any cross-linking agent containing one or more functional groups that can react with the anhydride groups of the PVM/MA copolymer can be used, advantageously a polyamine or a carbohydrate, such as an amino acid, a protein, an -ose, an -oside, etc., for example, lysine, arginine, histidine, hydrosoluble proteins, poly-L-lysine, poly-L-arginine, etc., preferably 1,3-diaminopropane.

Said empty nanoparticles may act as an adjuvant in vaccination or in immunotherapy when administered together with vaccines or compositions for immunotherapy (immunotherapeutic compositions) containing an antigen or an allergen, respectively, producing an immune response stimulating effect after the administration of the vaccine or of the immunotherapeutic composition and the empty nanoparticles. FIG.

12 shows how the administration of empty nanoparticles induces the secretion of significant amounts of IFN-γ. The combined administration of a vaccine or of an immunotherapeutic composition and the nanoparticles can be done simultaneously or sequentially, at different times, in any order, i.e. first the vaccine or immunotherapeutic composition can be administered, and then the nanoparticles or vice versa. Alternatively, said vaccine or immunotherapeutic composition and said nanoparticles can be simultaneously administered. The vaccine or immunotherapeutic composition and the nanoparticles can also be administered in the same composition or in different compositions. The empty nanoparticle dose to be administered may vary within a broad interval, for example between about 0.01 and about 10 mg/kg of body weight, preferably between 0.1 and 2 mg/kg of body weight.

In another particular embodiment, the composition of the invention comprises PVM/MA-based nanoparticles loaded with an allergen or an antigen and/or with an immunostimulating agent.

In a variant of this invention, the composition of the invention comprises PVM/MA-based nanoparticles loaded with an allergen or with an antigen, where said PVM/MA-based nanoparticles comprise an allergen or an antigen.

As it is used in this description, the term "allergen" refers to a substance to which a subject is sensitive and which causes an immune reaction, for example allergenic pollen extracts, allergenic insect extracts, allergenic food or food product extracts, components present in saliva, insect pincers or stingers inducing a sensitivity reaction in a subject, components present in plants inducing a sensitivity reaction in a subject, etc. Therefore, for example, pollen protein extracts, such as grass pollen (*Lolium perenne, Poa pratense, Phleum pratense, Cynodon dactylon, Festuca pratensis, Dactylis glomerata, Secale cereale, Hordeum vulgare, Avena sativa, Triticum sativa*), extracts from other grasses (such as *Artemisia vulgaris, Chenopodium album, Plantago lanceolata, Taraxacum vulgare, Parietaria judaica, Salsola kali, Urtica dioica*), or tree pollen (such as *Olea europea, Platanus* sp., *Cupressus* sp.), etc., can be used. Insect protein extracts such as dust mite extracts (such as *Dermatophagoides pteronyssinus, Dermatophagoides farinae, Acarus siro, Blomia tropicalis, Euroglyphus maynei, Glyciphagus domesticus, Lepidoglyphus destructor, Tyrophagus putrescentiae*), etc., can also be used. Other allergen extracts can be obtained from fungi and animal epithelium (*Alternaria alternata, Cladosporium herbarum*, dog epithelium, cat epithelium, horse epithelium, feather mixture, *Penicillium notatum*, etc.), as well as from food components, etc. Virtually any allergen can be used in preparing allergen-loaded nanoparticles of the composition of the invention; nevertheless, in a particular embodiment, said allergen is ovalbumin (OVA), a protein that is widely used as an experimental allergenic model.

As it is used in this description, the term "antigen" refers to a native or recombinant immunogenic product obtained from a higher organism or from a microorganism, for example a bacteria, a virus, a parasite, a protozoa, a fungus, etc., containing one or more antigenic determinants, for example, structural components of said organism; toxins, for example exotoxins, etc. Practically, any antigen can be used in preparing the antigen-loaded nanoparticles of the composition of the invention; nevertheless, in a particular embodiment, said antigen is the HE extract of *Salmonella enteritidis*.

As is known, *Salmonella enteritidis* is the causal agent of human gastroenteritis most frequently detected in food poisoning (60% of the cases in which the agent has been able to be isolated). Poultry and poultry byproducts are recognized as the main reservoir of *Salmonella*, and the most important source of *Salmonella enteritidis* infection in humans. The infection is a zoonosis transmitted by ingesting contaminated foods or water, and it is currently a pandemia. To control salmonellosis, both the World Health Organization (WHO) and the European Union have established guidelines for monitoring and eradicating infection by *Salmonella enteritidis* in poultry, since the benefits for the human population are evident. Antibiotics, competitive exclusion, genetic selection of the birds and vaccines, as well as improved hygiene conditions of poultry breeding farms, have been used in poultry *Salmonella* control. Out of these measures, it is widely accepted that the most practical one would be vaccination, as it is the easiest and least costly measure to apply. Even though attenuated live vaccines and dead (bacterines) vaccines are currently being used, both are rather ineffective in poultry farms (chickens and other poultry species) [Zhang-Barber et al., *Vaccine*, 17 (1999) 2538-2545]. In addition to their little effectiveness, the great disadvantage of live vaccines is their virulence potential in immunodepressed animals, as well as their possible reversal to invasive states. Furthermore, they have to be administered parenterally and they interfere with the traditional serological diagnostic tests. Inactivated (bacterines) bacteria do not have risks of residual virulence, but they do not induce a cellular immune response. The administration of a potent adjuvant is required, and multiple booster doses are needed. An alternative would be the use of subcellular vaccines that are able to stimulate a suitable immune response against infection caused by *Salmonella enteritidis*. Even though a high degree of protection has been described for these vaccines at the experimental level, like bacterines, they require multiple booster doses in order to obtain an acceptable degree of protection [Powell, *Pharm Res*, 13 (1996) 1777-1785]. On the other hand, if they are orally administered they experience denaturation and degradation in the gastrointestinal tract [Langer et al., *Adv Drug Deliv. Rev*, 28 (1997) 97-119], so this type of vaccines must be administered parenterally, with the subsequent logistic and economic obstacles that this implies. *Salmonella enteritidis* antigens can be encapsulated in the PVM/MA nanoparticles hereinbefore described for the purpose of solving these drawbacks.

The allergen or antigen present in this variant of the composition of the invention may at least partially coat the surface of said nanoparticles and/or be contained inside said nanoparticles. In a particular embodiment, said allergen or antigen coats all or part of the surface of said nanoparticles. This embodiment is useful for selectively stimulating a Th2 response in the subject. In another particular embodiment, said allergen or antigen is encapsulated inside said PVM/MA nanoparticles. This embodiment is useful for stimulating a balanced Th1 and Th2 response, or with a predominating Th1 response.

PVM/MA nanoparticles loaded with an allergen or an antigen can easily be obtained by means of a process similar to that disclosed in patent application WO 02/069938. By way of illustration, said nanoparticles loaded with an allergen or with an antigen can be easily prepared by desolvation with a liquid phase, for example a hydroalcoholic phase, such as a liquid phase formed by ethanol and water, of a solution of a PVM/MA copolymer in an organic solvent, such as a polar organic solvent, for example acetone. The formed nanoparticles are left in aqueous suspension or are lyophilized. Depending on the moment in which the allergen or the antigen is added, different formulations will be obtained with different arrangements of the allergen or antigen (see the formulations identified as NP I, NP II, NP III, NP IV and NP HE 3934 in Examples 1 and 6). By way of illustration, when it is desirable for the allergen or antigen to coat all or part of the nanoparticle surface, then said allergen or said antigen is incubated after having evaporated the organic solvents. Likewise, when it is desirable that the allergen or antigen is encapsulated inside said nanoparticles, then said allergen or said antigen is incubated, which allergen or antigen is dispersed in a solvent, preferably the solvent in which the PVM/MA copolymer solution is found, or is miscible with said solvent, such as a preferably polar organic solvent, or a solvent miscible with the solvent of the polymer solution, for example acetone, before adding said liquid phase used to desolvate the PVM/MA copolymer solution. If desired, a cross-linking agent may optionally be added, as hereinbefore mentioned in relation to empty nanoparticles.

More specifically, in another aspect the invention relates to a process for producing a composition of the invention comprising PVM/MA copolymer nanoparticles loaded with an allergen or with an antigen, where said PVM/MA copolymer nanoparticles comprise an allergen or an antigen, said process comprising the steps of:

a) desolvating an organic solution of a PVM/MA copolymer dissolved in an organic solvent with a hydroalcoholic solution;
b) removing the organic solvents to obtain nanoparticles; and
c) adding said allergen or said antigen to said PVM/MA copolymer organic solution before desolvating said PVM/MA copolymer organic solution or alternatively incubating said allergen or said antigen with said nanoparticles obtained in step b).

The organic solvent in which the PVM/MA copolymer is dissolved can be any solvent in which said copolymer is soluble, typically a polar solvent, such as a ketone, for example acetone. The liquid phase used to perform said desolvation can be any hydroalcoholic solution comprising alcohol and water, for example ethanol and water, for example alcohol and pharmaceutical grade water (purified water or water for injection, according to the application). Advantageously, the copolymer solution:hydroalcoholic solution ratio is comprised between 1:1 and 1:10, preferably 1:4. Then the organic solvents are removed by any conventional method, for example by means of evaporation at reduced pressure, and the nanoparticles are instantly formed in the medium, under the occurrence of a stable aqueous milky suspension.

The addition of the allergen or the antigen to the PVM/MA copolymer organic solution before desolvating said PVM/MA copolymer organic solution allows obtaining nanoparticles in which the allergen or the antigen is contained inside said nanoparticles. Advantageously, said allergen or antigen is added, dissolved or dispersed in the same organic solvent as that of the PVM/MA copolymer organic solution, or else miscible with said solvent, such as a polar organic solvent, for example acetone. Alternatively, the incubation of said allergen or of said antigen with the nanoparticles obtained in step b) allows obtaining nanoparticles in which the allergen or antigen coats all or part of the outer surface of said nanoparticles. In a particular embodiment, incubation of the allergen or antigen with the nanoparticles is done in an aqueous medium.

If desired, a cross-linking agent may optionally be added to improve nanoparticle stability, as hereinbefore described in relation to the empty nanoparticles.

The obtained nanoparticles loaded with allergen or antigen can be purified by conventional means, for example by means of centrifugation, ultracentrifugation, tangential filtration or evaporation, including the use of vacuum.

Finally, if desired, nanoparticles loaded with allergen or antigen can be lyophilized for their long-term storage and preservation. Standard cryoprotective agents can be used, preferably at a concentration comprised between 0.1 and 10% by weight with respect to the total composition weight, to facilitate lyophilization.

Nanoparticles loaded with allergen or antigen can act as an adjuvant in vaccination or immunotherapy and produce an immune response stimulating effect after their administration to a subject, as is shown in Examples 3-6.

The doses of nanoparticles loaded with allergen or antigen to be administered may vary within a wide range, for example between about 0.01 and about 10 mg/kg of body weight, preferably, between 0.1 and 2 mg/kg of body weight.

In another variant of this invention, the composition of the invention comprises PVM/MA-based nanoparticles loaded with an immunostimulating agent, where said PVM/MA-based nanoparticles comprise an immunostimulating agent.

As it is used in this description, the term "immunostimulating agent" or "immunomodulator" refers to a product that is able to specifically or non-specifically enhance immune response, for example, proteins or peptides working as natural adjuvants stimulating immune system response to the allergen or antigen, bacterial lipopolysaccharides, components of the cell wall of Gram-positive bacteria (for example muramyl dipeptide (MDP)), DNA CpG sequences, plant extracts, mainly saponin plant extracts, etc. Virtually any immunostimulating agent can be used in preparing immunostimulating agent-loaded nanoparticles of the composition of the invention; nevertheless, in a particular embodiment, said immunostimulating agent is the rough lipopolysaccharide of *Brucella ovis*.

Said immunostimulating agent may at least partially be coating the surface of said nanoparticles and/or contained inside said nanoparticles. In a particular embodiment, said immunostimulating agent coats all or part of the surface of said PVM/MA nanoparticles, whereas in another particular embodiment, said immunostimulating agent is encapsulated inside said PVM/MA nanoparticles.

The PVM/MA nanoparticles loaded with immunostimulating agent can easily be obtained by means of a process similar to that hereinbefore described in relation to preparing PVM/MA nanoparticles loaded with an allergen or with an antigen, but replacing said allergen or antigen with the immunostimulating agent. Thus, depending on the moment in which the immunostimulating agent is added, different formulations will be obtained with different arrangements thereof (see Example 1 or 4). By way of illustration, when it is desirable for the immunostimulating agent to coat all or part of the nanoparticle surface, then said immunostimulating agent is incubated after having evaporated the organic solvents. Likewise, when it is desirable that the immunostimulating agent is encapsulated inside said nanoparticles, then said immunostimulating agent is incubated, which agent is dispersed or dissolved in a solvent, advantageously the solvent in which the PVM/MA copolymer solution is found, or is miscible with said solvent, such as a preferably polar organic solvent, or a solvent miscible with the solvent of the polymer solution, for example acetone, before adding said liquid phase used to desolvate the PVM/MA copolymer solution. If desired, a cross-linking agent may optionally be added, as hereinbefore mentioned in relation to the empty nanoparticles.

If desired, a cross-linking agent may optionally be added to improve nanoparticle stability, as hereinbefore described in relation to the empty nanoparticles.

Nanoparticles loaded with immunostimulating agent can be purified by conventional means as hereinbefore mentioned in relation to the nanoparticles loaded with allergen or antigen. If so desired, the nanoparticles loaded with immunostimulating agent can also be lyophilized using standard cryoprotective agents, preferably at a concentration comprised between 0.1 and 10% by weight with respect to the total composition weight.

Nanoparticles loaded with immunostimulating agent can act as an adjuvant in vaccination or immunotherapy and produce an immune response stimulating effect after their administration to a subject.

The dose of nanoparticles loaded with immunostimulating agent to be administered may vary within a broad range, for example between about 0.01 and about 10 mg/kg of body weight, preferably between 0.1 and 2 mg/kg of body weight.

In another variant of this invention, the composition of the invention comprises PVM/MA nanoparticles loaded with an allergen or an antigen and with an immunostimulating agent, where said PVM/MA nanoparticles comprise an allergen or an antigen and an immunostimulating agent.

The allergen or antigen as well as the stimulating agent present in this variant of the composition of the invention may at least partially coat the surface of said nanoparticles and/or be contained inside said nanoparticles.

In a particular embodiment, said allergen or antigen coats all or part of the surface of said nanoparticles, whereas the immunostimulating agent is contained inside said nanoparticles, having found that this particular embodiment allows selectively stimulating a Th2 response in the subject.

In another particular embodiment, said allergen or antigen is encapsulated inside said PVM/MA nanoparticles, whereas said stimulating agent at least partially coats the surface of said nanoparticles. This embodiment is particularly interesting for stimulating a balanced Th1 and Th2 response, or predominantly a Th1 response.

In another particular embodiment, both the allergen or antigen and the immunostimulating agent are encapsulated inside said PVM/MA nanoparticles.

PVM/MA nanoparticles containing an allergen or an antigen and an immunostimulating agent can be easily obtained by means of a process similar to those hereinbefore described. Depending on the moment at which the allergen or the antigen and the immunostimulating agent are added, different formulations will be obtained with different arrangements of said products. By way of illustration, when it is desirable for the immunostimulating agent to coat all or part of the nanoparticle surface, then said immunostimulating agent is incubated after having evaporated the organic solvents. Likewise, when it is desirable that the immunostimulating agent is encapsulated inside said nanoparticles, then said immunostimulating agent is incubated, which immunostimulating agent is dispersed or dissolved in a solvent, advantageously the solvent in which the PVM/MA copolymer solution is found, or is miscible with said solvent, such as a preferably polar organic solvent, or a solvent miscible with the solvent of the polymer solution, for example acetone, before adding said liquid phase used to desolvate the PVM/MA copolymer solution. Similarly, when it is desirable for the allergen or antigen to coat all or part of the nanoparticle surface, then said allergen or said antigen is incubated after having evaporated the organic solvents. Likewise, when it is desirable that the allergen or antigen is encapsulated inside said nanoparticles, then said allergen or antigen is incubated, which allergen or antigen is dispersed or dissolved in a solvent, advantageously the solvent in which the PVM/MA copolymer solution is found, or is miscible with said solvent, such as a preferably polar organic solvent, or a solvent miscible with the solvent of the polymer solution, for example acetone, before adding said liquid phase used to desolvate the PVM/MA copolymer solution. Similarly, when it is desirable for the allergen or antigen and the immunostimulating agent to be encapsulated inside said nanoparticles, then said allergen or said antigen is incubated, optionally mixed with said immunostimulating agent, which is dispersed or dissolved in a solvent, advantageously the solvent in which the PVM/MA copolymer solution is found, or is miscible with said solvent, such as a preferably polar organic solvent, or a solvent miscible with the solvent of the polymer solution, for example acetone, before adding said liquid phase used to desolvate the PVM/MA copolymer solution. In any case, if so desired a cross-linking agent may optionally be added to the obtained nanoparticles to improve their stability, as hereinbefore described in relation to the empty nanoparticles.

More specifically, in another aspect, the invention relates to a process for producing a composition of the invention comprising PVM/MA copolymer nanoparticles loaded with an allergen or with an antigen and with an immunostimulating agent, where said PVM/MA copolymer nanoparticles comprise an allergen or an antigen and an immunostimulating agent, said process comprising the steps of:

a) desolvating an organic solution of a PVM/MA copolymer dissolved in an organic solvent with a hydroalcoholic solution;

b) removing the organic solvents to obtain nanoparticles; and c) adding said allergen or said antigen and/or said immunostimulating agent to said PVM/MA copolymer organic solution before desolvating the PVM/MA copolymer organic solution, or alternatively incubating said allergen or said antigen or said immunostimulating agent with said nanoparticles obtained in step b).

Steps a) and b) are carried out in a manner similar to that hereinbefore described in relation to the process for producing a composition of the invention comprising PVM/MA copolymer nanoparticles loaded with an allergen or with an antigen. Step c) is carried out in a manner similar to that hereinbefore described in relation to said process, however making the corresponding modifications for adding the immunostimulating agent, either to said PVM/MA copolymer organic solution before desolvating said PVM/MA copolymer organic solution, optionally with the allergen or antigen, or alternatively incubating said immunostimulating agent with said nanoparticles obtained in step b), optionally partially coated with said allergen or antigen, according to that discussed above.

If so desired, a cross-linking agent may optionally be added to improve the stability of the obtained nanoparticles. The obtained nanoparticles loaded with allergen or antigen and with immunostimulating agent can be purified by conventional means, for example by means of centrifugation, ultracentrifugation, tangential filtration or evaporation, including the use of a vacuum.

Finally, if so desired, the nanoparticles loaded with allergen or antigen can be lyophilized for their long-term storage and preservation. Standard cryoprotective agents can be used, preferably at a concentration comprised between 0.1 and 10% by weight with respect to the total composition weight, to facilitate lyophilization.

The nanoparticles loaded with an allergen or with an antigen and with an immunostimulating agent can act as an adjuvant in vaccination or immunotherapy and produce an immune response stimulating effect after their administration to a subject, as is shown in Examples 3-6.

The dose of nanoparticles loaded with an allergen or an antigen and with an immunostimulating agent to be administered may vary within a broad range, for example between about 0.01 and about 10 mg/kg of body weight, preferably between 0.1 and 2 mg/kg of body weight.

If so desired, the composition of the invention can be in the lyophilized form or in a suitable administration form for its oral or parenteral administration. Lyophilization is carried out by conventional methods, optionally in the presence of conventional cryoprotective agents, for example sucrose, mannitol, trehalose, glycerol, lactose, sorbitol, polyvinylpyrrolidone, etc., preferably at a concentration comprised between 0.1 and 10% by weight with respect to total composition weight. In order to manufacture the different administration forms suitable for their oral or parenteral administration, acceptable excipients and carriers suitable for manufacturing the desired administration pharmaceutical form will be used. Information on said carriers and excipients, as well as information on said suitable administration forms for the oral or parenteral administration of the composition of the invention can be found in Galenic pharmacy treatises.

As previously mentioned, the composition of the invention produces an immune response stimulating or enhancing effect after its administration to a subject, so it can be used as an adjuvant in vaccines or immunotherapy. In fact, the composition of the invention has the ability to selectively stimulate one of the two immune response pathways (Th1 or Th2) or else both pathways in a simultaneous and balanced manner, so it can be used in vaccine or immunotherapeutic formulations, according to the response that is to be stimulated. By way of illustration, depending on the mechanisms of pathogenicity of the organism from which the antigen originates (intracellular or extracellular, dependent toxin, dependent flagellum, etc.), stimulation of the Th1 response (intracellular, as in the case of *Brucella, Salmonella*, etc.) or the Th2 response (extracellular, as in the case of *Staphylococcus, Escherichia coli*, enterotoxigenic bacteria, etc.) is generally required for a vaccine formulation. Likewise, by way of illustration, tolerance induction is required for an immunotherapeutic formulation by the presence of the two response types, i.e. inducing Th1 and Th2 responses in a balanced manner. Generally, to stimulate a selective Th2 response, the formulations will contain PVM/MA nanoparticles completely or partially coated with the allergen or antigen, whereas to stimulate a Th1 and Th2 response in a balanced manner, or with a Th1 response predominance, the formulations will contain PVM/MA nanoparticles in which the antigen or allergen will be encapsulated and said nanoparticles will advantageously include a cross-linking agent. In any of the previously mentioned cases, the nanoparticles may include an immunostimulating agent if so desired.

Therefore, in another aspect, the invention relates to a vaccine or an immunotherapy composition comprising a therapeutically effective amount of an immune response stimulating composition (composition of the invention) together with a pharmaceutically acceptable carrier or excipient. Said vaccine or immunotherapy composition may be in any pharmaceutical administration form to be administered by any route, for example orally, parenterally, rectally, etc. In a particular embodiment, said vaccine or immunotherapy composition is in an oral administration pharmaceutical form, whereas in another particular embodiment, said vaccine or immunotherapy composition is in a parenteral administration pharmaceutical form, for example intramuscular (i.m.), subcutaneous (s.c.), intravenous (i.v.), intraperitoneal (i.p.), intradermal (i.d.), etc. A review of the different administration dosage forms for drugs in general and the processes for the manufacture thereof can be found in the book "Tratado de Farmacia Galénica", by C. Faulí i Trillo, $1^{st}$ Edition, 1993, Luzán 5, S. A. de Ediciones.

The composition of the invention present in said immunotherapy vaccine or composition provided by this invention comprises PVM/MA nanoparticles. Said nanoparticles may further contain an allergen or an antigen and/or an immunostimulating agent, which may be contained inside said nanoparticles and/or at least partially coating the surface of said nanoparticles. Likewise, said nanoparticles may optionally contain a cross-linking agent.

In a particular embodiment, the composition of the invention present in said vaccine or immunotherapy composition provided by this invention comprises empty PVM/MA nanoparticles optionally incorporating a cross-linking agent. In this case, the composition of the invention is administered in combination with vaccine or immunotherapeutic compositions containing an antigen or an allergen, respectively, producing an immune response stimulating effect after the administration of said vaccine or immunotherapeutic composition and the empty nanoparticles. The combined administration of said vaccine or immunotherapeutic composition and of the empty nanoparticles can be done simultaneously or sequentially, at different times, in any order, i.e. first the vaccine or immunotherapeutic composition can be administered, and then the empty nanoparticles or vice versa. Alternatively, said vaccine or immunotherapeutic composition and said empty nanoparticles can be simultaneously administered. In this case, the vaccine or immunotherapeutic composition and the empty nanoparticles can be administered in the same composition or in different compositions.

In another particular embodiment, the composition of the invention present in said immunotherapy vaccine or composition provided by this invention comprises PVM/MA nanoparticles where said PVM/MA nanoparticles further comprise an allergen or an antigen, and a cross-linking agent if so desired.

In another particular embodiment, the composition of the invention present in said immunotherapy vaccine or composition provided by this invention comprises PVM/MA nanoparticles where said PVM/MA nanoparticles further comprise an immunostimulating agent, and a cross-linking agent if so desired.

In another particular embodiment, the composition of the invention present in said immunotherapy vaccine or composition provided by this invention comprises PVM/MA nanoparticles where said PVM/MA nanoparticles further comprise an allergen or an antigen and an immunostimulating agent, and a cross-linking agent if so desired.

The immunotherapy vaccine or composition provided by this invention comprises a composition of the invention in a therapeutically effective amount, i.e. in an amount that is suitable for enhancing or stimulating immune response. Therefore, the amount of composition of the invention present in a vaccine or immunotherapy composition provided by this invention may vary within a broad range, depending on, among other factors, the type of nanoparticles (empty or loaded with allergen or antigens and/or with immunostimulating agent), etc. Nevertheless, in a particular embodiment, the invention provides a vaccine or immunotherapy composition comprising:

| Component | % by weight with respect to total |
| --- | --- |
| PVM/MA nanoparticles | 84-99.998% |
| Cross-linking agent | 0.001-1% |
| Allergen or antigen | 0.001-15% |

Said immunotherapy vaccine or composition may optionally contain a cryoprotective agent in a sufficient amount to protect the nanoparticles during the lyophilization process.

In a particular embodiment, said allergen comprises an allergenic pollen extract, an allergenic insect extract or an allergenic food product extract.

In another particular embodiment, said antigen comprises an immunogenic extract from an organism, for example a *Salmonella* spp membrane extract.

As previously mentioned, the composition of the invention has the capacity to produce an immune response stimulating or enhancing effect after its administration to a subject, so it can be used as an adjuvant in vaccines or immunotherapy, and more specifically it has the ability to selectively stimulate one of the two immune response pathways (Th1 or Th2) or even both pathways in a simultaneous and balanced manner.

Therefore, in another aspect the invention relates to the use of a composition of the invention in the manufacture of a vaccine or immunotherapy composition.

In another aspect, the invention relates to the use of a composition of the invention in the manufacture of a pharmaceutical composition for the selective or predominant stimulation or enhancement of the Th1 immune response.

In another aspect, the invention relates to the use of a composition of the invention in the manufacture of a pharmaceutical composition for the selective or predominant stimulation or enhancement of the Th2 immune response.

In another aspect, the invention relates to the use of a composition of the invention in the manufacture of a pharmaceutical composition for the balanced stimulation or enhancement of the Th1 and Th2 immune responses.

The use of the composition of the invention for vaccination and immunotherapy has several advantages as it comprises:
- using pharmaceutical forms that are biodegradable in normal conditions of the organism, and that are manufactured from polymers and materials accepted in pharmaceutical and medical practice;
- administering a nanoparticle-based immunotherapy and vaccination preparation which protects the encapsulated allergen or antigen from its premature inactivation;
- manufacturing an immunotherapy and vaccine preparation, based on using nanoparticles, which shows sustained release over time; the period of time during which the controlled release will occur will depend on the microenvironmental conditions belonging to the administration site;
- administering a nanoparticulate adjuvant based on nanoparticles, given their characteristics (innocuousness, biodegradability, avirulence), may be susceptible to use in humans and animals for immunotherapeutic and vaccination purposes through different administration routes; and
- administering a nanoparticulate adjuvant based on nanoparticles, which, given their bioadhesive potential in the gastrointestinal tract, makes oral administration a possible administration route.

The following examples illustrate the invention and must not be considered to be limiting thereof.

EXAMPLES

The following examples describe the production of different types of PVM/MA-based nanoparticles which, optionally, contain allergens or antigens and/or an immunostimulating agent, and they manifest the capacity of said nanoparticles to act as adjuvant in immunotherapy or vaccination.

General Nanoparticle Production Process

The general PVM/MA nanoparticle production process comprises dissolving said copolymer in acetone followed by the addition of ethanol. A similar volume of water is added to the resulting solution, such that the nanoparticles are instantly formed in the middle, under the appearance of a milky suspension. Then, the organic solvents (ethanol and acetone) are removed by means of evaporation under reduced pressure, the particles remaining in a stable aqueous suspension [Arbos et al, *J Control Rel*, 83 (2002) 321-330]. Depending on the moment in which the allergens or antigens are added, and when applicable, the immunostimulating agent, different formulations will be obtained with different arrangements thereof (see Examples 1, 5 and 6). As an example:

A. In order to obtain formulations containing the allergen or the antigen encapsulated inside the nanoparticles (formulations NP I and NP VI): incubation with the allergen or antigen to be encapsulated is performed after having evaporated the organic solvents.

B. In order to obtain formulations containing the allergen or the antigen totally or partially coating the outer surface of the nanoparticles (formulations NP II, NP III, NP IV, NP V, NP VII, OVASAL and NP HE): the allergen or antigen is incubated dispersed in acetone before adding the ethanol and the water.

The next step consists of adding the cross-linking agent which, in this case, was 1,3-diaminopropane, to formulations NP III, NP V, NP VII, OVASAL, NP HE (5 µg/mg of polymer in all of them) and NP IV (10 µg/mg polymer).

Formulations NP-V, NP-VI and NP-VII contain an immunostimulating agent consisting of the rough lipopolysaccharide (R-LPS) of *Brucilla ovis*. Briefly, for it to be incorporated, in the case of formulation NP V, incubation with said immunostimulating agent is carried out after having evaporated the organic solvents, whereas in the case of formulations NP VI and NP VII the R-LPS is incubated before adding the ethanol and the water (see Examples 1.4.2, 1.4.3 and 1.4.4).

Nanoparticle purification is carried out by means of ultracentrifugation. Finally, the purified nanoparticles are lyophilized for their long-term storage and preservation.

Nanoparticle Characterization

Nanoparticle size and zeta potential were determined in a Zetamaster (Malvern Instruments/Optilas, Spain).

Encapsulated protein content (active ingredient) was determined by means of the microbicinchoninic acid protein assay (Micro BCA, Pierce, USA).

The rough lipopolysaccharide of *Brucella ovis* (R-LPS) adsorbed or encapsulated in the nanoparticles was quantified indirectly by measuring one of its exclusive markers, KDO (3-deoxy-D-manno-oct-2-ulosonic acid), by the thiobarbituric acid method [Warren, J Biol Chem, 243 (1959) 1971-1975].

Anti-OVA, Cytokine and IL-10 Antibody Determination

Serum anti-OVA antibodies were analyzed by ELISA with anti-$IgG_1$ and anti-$IgG_{2a}$ conjugates (Sigma-Aldrich Chemie, Germany). Briefly, to carry out this assay 96-well plates (EB, Thermo Labsystems, Vantaa, Finland) were used in which 1 μg of ovalbumin per well was fixed at 4° C. for 15 hours; subsequently 5 washings of 1 minute each were performed in an ELISA washer (Thermo Labsystems, Vantaa, Finland), the serums were added in serial dilutions starting from 1:40, they were incubated at 37° C. for 4 hours and 5 washings of 1 minute were subsequently performed; the conjugate was then incubated for 2 hours with peroxidase, a further 5 washings of 1 minute were performed, the substrate [ABTS (2,2'-azino-bis(3-ethylbenzene-thiazoline-6-sulfonic acid) (Sigma-Aldrich Chemie, Germany)] was added and the reading was performed at 405 nm in a plate reader (iEMS Reader MF, Labsystems, Vantaa, Finland) after 30 minutes of incubation at room temperature.

The cytokines (IFN-γ, IL-4) were analyzed by ELISA kits (Biosource, USA) in the supernatants originating from spleen cell restimulation of previously immunized mice.

IL-10 was analyzed in serums from blood previously centrifuged at 800×g for 10 minutes, by an ELISA kit (Biosource, USA).

Sodium Dodecylsulfate Polyacrylamide Gel Electrophoresis (SDS-PAGE)

The protein profile of the samples was determined by SDS-PAGE [Laemmli, Nature, 227 (1970) 680-685], at a 15% concentration of 37.5:1 acrylamide:bisacrylamide (Biorad), in 125 mM Tris-HCl (pH 6.8) and 0.1% SDS in the gel. The electrode buffer used contained 30 mM Tris-HCl (pH 8.3), 192 mM glycine and 0.1% SDS. The sample was treated at 100° C. for 10 minutes in 62.5 mM Tris-HCl (pH 6.8), 10% glycerol, 2% SDS, 5% β-mercaptoethanol and 0.002% bromophenol blue. Electrophoresis was performed in 8×7 cm gels with a constant intensity of 15 mA/gel. The gels were stained with Coomassie blue [King, Anal Biochem, 71 (1976) 223-230]. To this end they were incubated in 3% trichloroacetic acid in water for 1 hour for their fixing. Staining was performed with a 0.25% Coomassie blue solution in 50% methanol and 10% acetic acid for 1 hour and it was discolored in 50% methanol and 20% acetic acid until the samples were made visible. The apparent molecular weights of the sample components were determined comparing their electrophoretic mobility with a standard molecular weight marker (Rainbow, Amersham Pharmacia Biotech, Uppsala, Sweden) containing myosin (220 kDa), phosphorylase b (97 kDa), bovine serum albumin (66 kDa), ovalbumin (45 kDa), carbonic anhydrase (30 kDa), trypsin inhibitor (20.1 kDa) and lysozyme (14.3 kDa).

Immunoblotting

Immunoblotting was performed according to a previously described protocol

[Towbin & Staehelin, Proc Natl Acad Sci USA, 76 (1979) 4350-4354]. Briefly, after subjecting the samples to SDS-PAGE, the gels were transferred to 0.45 μm pore size nitrocellulose membranes (Schleicher & Schuell, Dassel, Germany). The transfer was performed using the semi-dry method by means of the Trans-Blot® SD, Semy-Dry transfer Cell system (Bio-Rad, Richmond, USA) at 200 mA, 5 V for 30 minutes, in a transfer buffer of 25 mM Tris-HCl (pH 8.3), 192 mM glycine and 10% methanol.

Example 1

Immunotherapy

Preparation and Characterization of Ovalbumin the Methyl Vinyl Ether-Maleic Anhydride (PVM/MA) Copolymer-Based Nanoparticles The protein chosen was ovalbumin (OVA) since it is currently widely used as an experimental allergenic model.

Ovalbumin represents over 50% of the protein content of egg whites. It is a monomeric phosphoglycoprotein having 385 amino acids, with a molecular weight of 43 to 45 kDa [Johnsen and Elsayed, Mol Immunol, 27 (1990) 821]. Ovalbumin is the egg protein having greatest allergenic capability, immediately inducing type I hypersensitivity mediated by IgE.

The process described below is valid for preparing nanoparticle-type colloidal dosage forms that can be used for immunotherapy.

1.1 Preparation of Empty Nanoparticles (NP)

100 mg of the methyl vinyl ether-maleic anhydride copolymer (PVM/MA) [Gantrez® AN 119] are dissolved in 5 mL of acetone. Subsequently, 10 mL of ethanol and 10 mL of deionized water are added to this phase with magnetic stirring. The resulting mixture is allowed to homogenize for 5 minutes. The nanoparticle suspension is then evaporated under reduced pressure until both organic solvents are removed and the final volume is adjusted with water to 10 mL.

The solution is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained empty nanoparticles (NP) have a mean size of less than 200 nm and a net surface charge of −45.1 mV (see Table 1).

1.2 Preparation of Ovalbumin-Coated Nanoparticles (NP I)

100 mg of the methyl vinyl ether-maleic anhydride copolymer (PVM/MA) [Gantrez® AN 119] are dissolved in 5 mL of acetone. Subsequently, 10 mL of ethanol and 10 mL of deionized water are added to this phase under magnetic stirring. The resulting mixture is allowed to homogenize for 5 minutes. The nanoparticle suspension is then evaporated under reduced pressure until both organic solvents are removed and the final volume is adjusted with water to 5 mL. This solution is incubated for 1 hour at room temperature with 5 mL of an aqueous solution of ovalbumin containing 10 mg of protein.

The mixture is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained nanoparticles (NP I) have a mean size of less than 300 nm, a net surface charge of −61.3 mV and an ovalbumin content of 54.7 μg/mg of polymer (see Table 1).

1.3 Preparation of Nanoparticles With Encapsulated Ovalbumin (NP II, NP III and NP IV)

100 mg of the methyl vinyl ether-maleic anhydride copolymer (PVM/MA) [Gantrez® AN 119] are dissolved in 4 mL of acetone, whereas on the other hand 5 mg of ovalbumin are dispersed in 1 mL of acetone by ultrasonication (Microson™) or ultrasonic bath for 1 minute with cooling. The ovalbumin dispersion is added to the polymer suspension and is stirred for 30 minutes at room temperature. Subsequently, 10 mL of ethanol and 10 mL of deionized water are added to this phase with magnetic stirring. The resulting mixture is allowed to homogenize for 5 minutes. The nanoparticle suspension is then evaporated under reduced pressure until both organic solvents are removed and the final volume is adjusted with water to 10 mL. The obtained nanoparticles have encapsulated OVA (NP II). In the case of formulations NP III and NP IV the cross-linking agent would now be added: 0.05 mL and 0.1 mL of a 1% 1,3-diaminopropane solution, respectively.

The mixture is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained nanoparticles have a mean size of less than 300 nm, a net surface charge of −41.4 mV in the case of NP-II, −50.8 mV in NP-III and −57.5 mV in NP IV, and an ovalbumin content close to 30 µg/mg of polymer (see Table 1).

1.4 Preparation of Nanoparticles with Ovalbumin and *Brucella ovis* Rough Lipopolysaccharide (NP V, NP VI and NP VII)

1.4.1 Extraction and Characterization of the *Brucella ovis* Rough Lipopolysaccharide Complex The extract used is *Brucella ovis* rough lipopolysaccharide (R-LPS). R-LPS was obtained by a previously described method (Galanos et al, Eur. J. Biochem. (1969), 245-249). After culturing the bacteria, *Brucella ovis*, these are resuspended in absolute ethanol stirring at 4° C. overnight in a closed container. The cells are then centrifuged (6,000×g, 20 minutes, 4° C.) and resuspended in acetone stirring for 12 hour at 4° C. in a closed container. Subsequently, the cells are collected by centrifugation (6,000×g, 20 minutes, 4° C.), they are resuspended in ethyl ether and they are kept at room temperature from 3 to 4 hours with magnetic stirring. Then, they are centrifuged again (6,000×g, 20 minutes, 4° C.) and they are evaporated to dryness. In order to proceed to extraction the cells are mixed until homogenization with petroleum-chloroform-phenol ether at a ratio of 8:5:2 respectively. The mixture is centrifuged (8,000×g, 15 minutes, room temperature) and the supernatant is collected. The pellet is re-extracted under the same conditions two more times. All the supernatants are pooled and the petroleum and chloroform ethers are evaporated in a rotavapor. The phenolic residue is precipitated with distilled water and centrifuged (8,000×g, 30 minutes, room temperature). It is then washed two more times with phenol and twice again with ethyl ether. After the last centrifugation the ethyl ether remains are removed under vacuum, the pellet is resuspended in deionized water and it is dialyzed. Finally, the contents of the dialysis bag are centrifuged (100,000×g, 6 hours, 4° C.), the pellet is resuspended in deionized water and it is lyophilized.

The amount of R-LPS is determined indirectly by measuring one of its exclusive markers, KDO, by means of the thiobarbituric acid method.

1.4.2 Nanoparticles with Encapsulated Ovalbumin and *Brucella ovis* R-LPS on the Surface (NP V)

100 mg of the methyl vinyl ether-maleic anhydride copolymer [Gantrez® AN 119] are dissolved in 4 mL of acetone, whereas on the other hand 5 mg of ovalbumin are dispersed in 1 mL of acetone by ultrasonication (Microson™) or ultrasonic bath for 1 minute with cooling. The ovalbumin dispersion is added to the copolymer suspension and is stirred for 30 minutes at room temperature. Subsequently, 10 mL of ethanol and 10 mL of deionized water are added to this phase with magnetic stirring. The resulting mixture is allowed to homogenize for 5 minutes. The nanoparticle suspension is then evaporated under reduced pressure until both organic solvents are removed and the final volume is adjusted with water to 9 mL. This solution is incubated for 1 hour at room temperature with 1 mL of an aqueous dispersion (previously ultrasonicated for one minute) containing 1 mg of *Brucella ovis* R-LPS.

The mixture is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained nanoparticles (NP V) have a mean size of less than 300 nm, a net surface charge of −46.1 mV, an ovalbumin content of 64.1 µg/mg of polymer and 15.2 µg of R-LPS/mg of polymer (see Table 1).

1.4.3 Nanoparticles with Encapsulated *Brucella ovis* R-LPS and Ovalbumin on the Surface (NP VI)

100 mg of the methyl vinyl ether-maleic anhydride copolymer [Gantrez® AN 119] are dissolved in 4 mL of acetone, whereas on the other hand 1 mg of *Brucella ovis* R-LPS is dispersed in 1 mL of acetone by ultrasonication (Microson™) or ultrasonic bath for 1 minute with cooling. The R-LPS dispersion is added to the copolymer suspension and is stirred for 30 minutes at room temperature. Subsequently, 10 mL of ethanol and 10 mL of deionized water are added to this phase with magnetic stirring. The resulting mixture is allowed to homogenize for 5 minutes. The nanoparticle suspension is then evaporated under reduced pressure until both organic solvents are removed and the final volume is adjusted with water to 5 mL. This solution is incubated for 1 hour at room temperature with 5 mL of an aqueous solution containing 5 mg of ovalbumin.

The mixture is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained nanoparticles (NP VI) have a mean size of less than 300 nm and a net surface charge of −56.9 mV, an ovalbumin content of 68.5 µg/mg of polymer and 12.1 µg of R-LPS/mg of polymer (see Table 1).

1.4.4 Nanoparticles with Encapsulated Ovalbumin and *Brucella ovis* R-LPS (NP VII)

100 mg of the methyl vinyl ether-maleic anhydride copolymer [Gantrez® AN 119] are dissolved in 3 mL of acetone, whereas on the other hand 5 mg of ovalbumin are dispersed in 1 mL of acetone by ultrasonication (Microson™) or ultrasonic bath for 1 minute with cooling, and 1 mg of *Brucella ovis* R-LPS is dispersed in 1 mL of acetone, also by ultrasonication with cooling. The ovalbumin dispersion is added to the R-LPS dispersion, and this mixture is added to the copolymer suspension and stirred for 30 minutes at room temperature. Subsequently, 10 mL of ethanol and 10 mL of deionized water are added to this phase with magnetic stirring. The resulting mixture is allowed to homogenize for 5 minutes. The nanoparticle suspension is then evaporated under reduced pressure until both organic solvents are removed and the final volume is adjusted with water to 10 mL.

The mixture is subjected to purification by ultracentrifugation (20 minutes at 27,000×g). The supernatants are removed and the residue is resuspended in water or in a 5% sucrose aqueous solution. Finally, the resulting nanoparticle suspension is lyophilized, allowing it to maintain all its properties intact.

The obtained nanoparticles (NP VII) have a mean size of less than 300 nm and a net surface charge of −46.1 mV, an ovalbumin content of 54.7 μg/mg of polymer and 13.8 μg of R-LPS/mg of polymer (see Table 1).

1.5 Nanoparticle Characterization

The physicochemical characterization of the different formulations is shown in Table 1.

According to the results gathered it was observed that when the nanoparticles were coated with ovalbumin (NP I and NP VI) the size increases and the zeta potential becomes more negative, whereas if the ovalbumin is mostly inside the nanoparticles (NP II, NP III, NP IV, NP V and NP VII), the size, as well as the zeta potential, does not vary when compared to the empty nanoparticles (NP).

On the other hand it was observed that nanoparticle sizes increased as the amount of cross-linking agent added increased, and the amount of ovalbumin slightly decreased.

The presence of R-LPS on the nanoparticle surface makes the amount of encapsulated ovalbumin increase (NP V vs. NP II), whereas if the R-LPS is mostly inside the nanoparticles, the amount of adsorbed ovalbumin does not vary (NP VI vs. NP I).

TABLE 1

Physicochemical Characterization of the Different Formulations (with Data Expressed as Mean ± Standard Deviation, n = 10)

| | Size (nm) | Zeta potential (mV) | Encapsulated OVA (μg/mg) | Encapsulation effectiveness (%) | R-LPS (μg/mg) |
|---|---|---|---|---|---|
| NP | 158 ± 3 | −45.1 ± 0.5 | — | — | — |
| NP-I | 300 ± 4 | −61.3 ± 3.8 | 67.8 ± 20.2 | 47.50 ± 2.12 | — |
| NP-II | 205 ± 1 | −41.4 ± 2.5 | 36.1 ± 3.8 | 50.48 ± 5.32 | — |
| NP-III | 239 ± 4 | −50.8 ± 2.9 | 30.1 ± 4.5 | 42.14 ± 6.30 | — |
| NP-IV | 270 ± 2 | −57.5 ± 3.1 | 31.4 ± 4.2 | 44.08 ± 5.88 | — |
| NP-V | 152 | −46.1 | 64.1 ± 2.9 | 89.74 ± 4.06 | 15.2 ± 0.5 |
| NP-VI | 287 | −56.9 | 68.5 ± 2.4 | 47.95 ± 1.68 | 12.1 ± 0.6 |
| NP-VII | 135 | −43.7 | 54.7 ± 1.9 | 76.58 ± 2.66 | 13.8 ± 3.0 |

The production yield for the nanoparticles was about 70%.

Example 2

In Vitro Test of Ovalbumin Release from Nanoparticles

In order to evaluate in vitro ovalbumin release, the nanoparticles were incubated in 1 mL of PBS (Phosphate Buffered Saline, pH 7.4) in "eppendorf" tubes at an approximate concentration of 8 mg/mL. The tubes were incubated in an oven at 37° C. with rotation and at predetermined time intervals the samples were centrifuged at 26,500×g for 20 minutes, collecting the supernatant for its subsequent analysis. Released ovalbumin was measured in the supernatant by the bicinchoninic acid method.

The obtained ovalbumin release curve is shown in FIG. 1; it is observed that in formulation NP I the ovalbumin is released more quickly than in formulations NP II, NP III and NP IV, which show a similar release profile. This is because in formulation NP I the ovalbumin is adsorbed on the outside of the nanoparticles, so that its initial release (burst) is much more pronounced than that of the other formulations, in which part of the ovalbumin is encapsulated (NP II, III and IV). On the other hand, in the release profiles for NP II, NP III and NP IV it can be observed that as the amount of cross-linking agent increases, the percentage of released ovalbumin slightly decreases.

Example 3

Quantification of Anti-OVA Antibody Production after Immunization with Ovalbumin in BALB/c Mice 65 BALB/c mice were immunized, dividing them into 13 groups according to the administration regimen.

The controls used were free ovalbumin solution (OVA) (10 μg intradermally and 25 μg orally), empty nanoparticles (NP) (intradermally and orally) and ovalbumin adsorbed onto alhydrogel (OVA-Alum) (10 μg intradermally), as a Th2 response-inducing positive control, characterized by high $IgG_1$ titers [Faquim-Mauro et al, *Int Immunol*, 12 (2000) 1733-1740].

The remaining groups were inoculated intradermally (10 μg OVA) or orally (25 μg OVA), the different treatments being:

a) Ovalbumin (OVA) solution intradermally
b) Ovalbumin (OVA) solution orally
c) Ovalbumin absorbed onto alhydrogel (OVA-Alum) intradermally
d) Empty nanoparticles (NP) intradermally
e) Empty nanoparticles (NP) orally
f) Ovalbumin-coated nanoparticles (NP I) intradermally
g) Ovalbumin-coated nanoparticles (NP I) orally
h) Nanoparticles with encapsulated ovalbumin (NP II) intradermally
i) Nanoparticles with encapsulated ovalbumin (NP II) orally
j) Nanoparticles cross-linked with 1,3-diaminopropane with encapsulated ovalbumin (NP III and NP IV) intradermally
k) Nanoparticles cross-linked with 1,3-diaminopropane with encapsulated ovalbumin (NP III and NP IV) orally Successive blood extractions were performed on days 7, 14, 28 and 35 after immunization. The serums for each group were pooled and frozen at −80° C. for their subsequent analysis.

Figure 2:
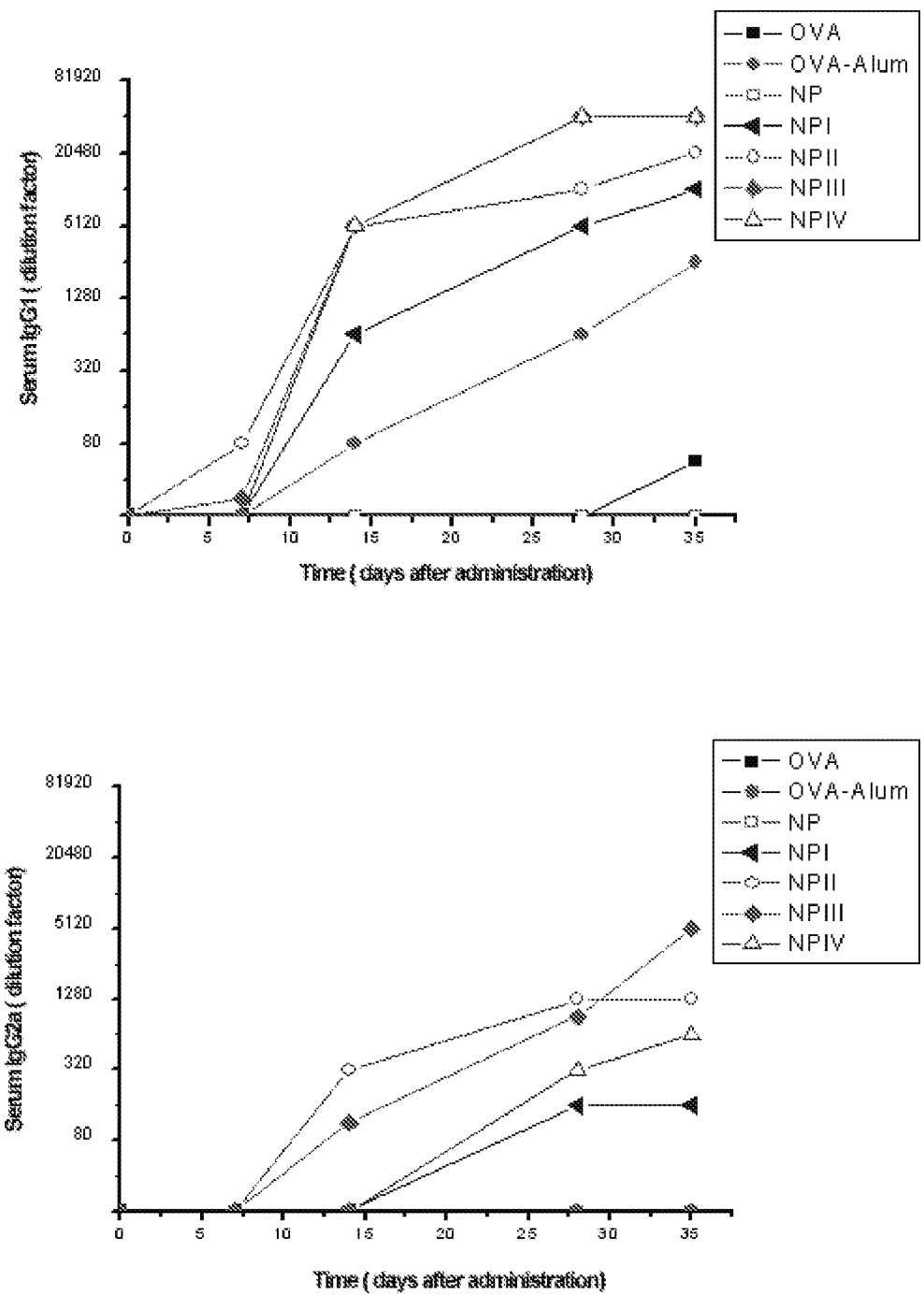
FIG. 2 shows a graph representing the levels of specific anti-ovalbumin antibodies ($IgG_1$, $IgG_{2a}$) after intradermally immunizing Balb/c mice with an ovalbumin (OVA)-free solution, ovalbumin adsorbed in alhydrogel (OVA-Alum), and empty nanoparticles (NP), NP-I, NP-II, NP-III and NP-IV over time.
Figure 3:
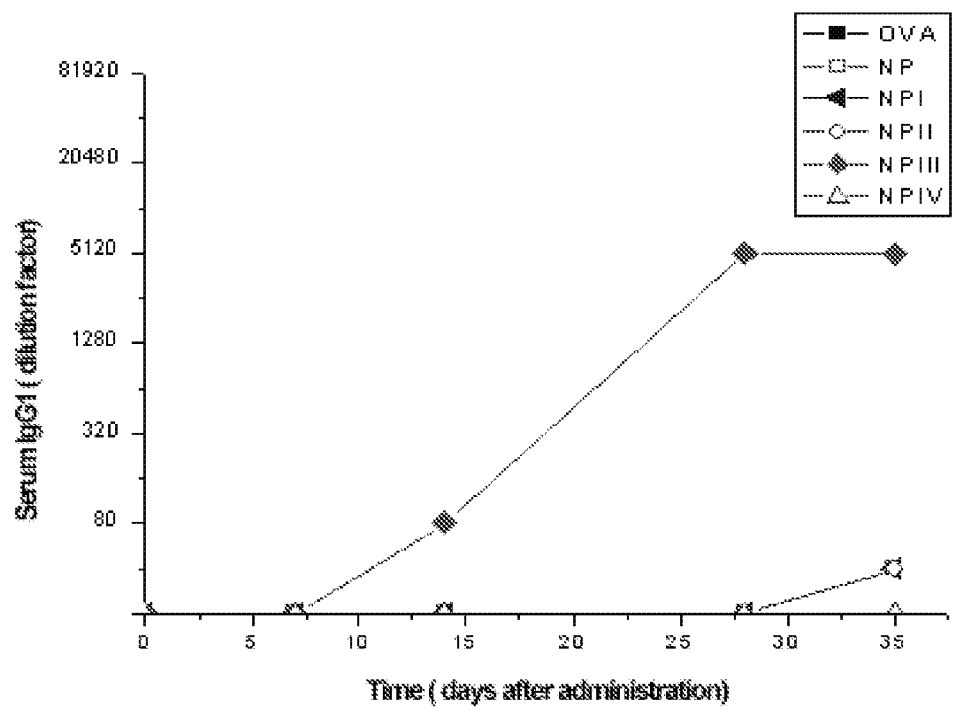
FIG. 3 shows a graph representing the levels of specific anti-ovalbumin antibodies ($IgG_1$, $IgG_{2a}$) after orally immunizing Balb/c mice with an ovalbumin (OVA)-free solution, and empty nanoparticles (NP), NP-I, NP-II, NP-III and NP-IV over time.
Figure 3:
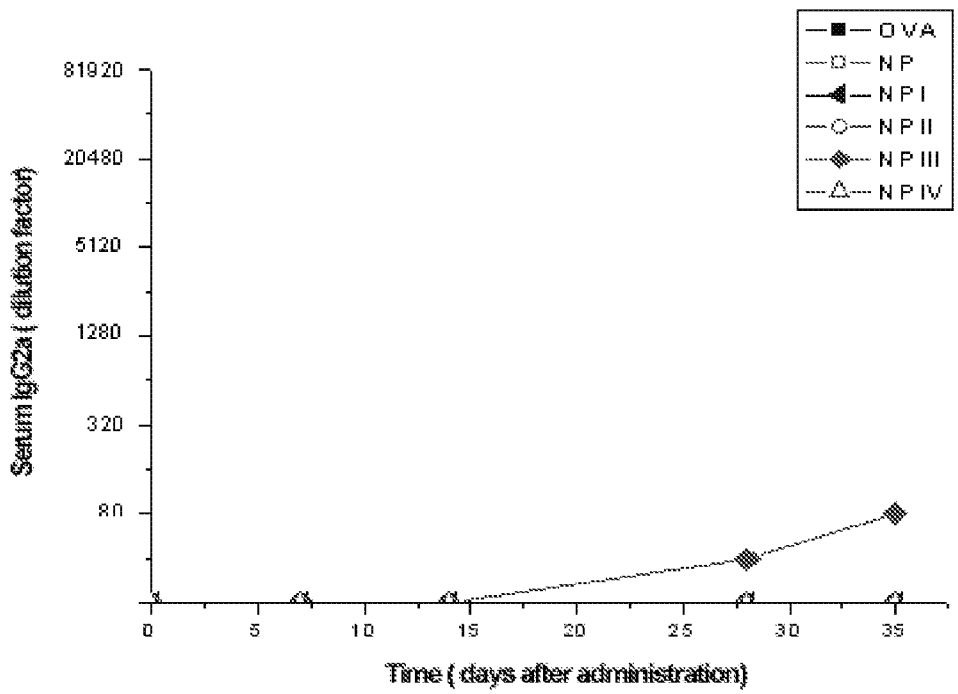

The levels of anti-OVA antibodies ($IgG_1$ and $IgG_{2a}$) were determined in the different serums by means of ELISA and the data shown in FIGS. 2 and 3 was obtained. It was observed that the nanoparticles that contained ovalbumin (NP I, NP II, NP III and NP IV) either coating the nanoparticles or encapsulated therein, increased the immune response with respect to ovalbumin in solution. On day 14 after administration, said nanoparticle formulations are able to increase $IgG_1$ titer in mice serums by 3 or 6 logarithmic units, depending on the type. On the other hand, mice administered OVA-Alum had an absence of serum $IgG_{2a}$ antibodies during the entire experiment, whereas mice administered NP III reached a titer of 5120 on day 35 after immunization.

This indicates that, in general, said NP formulations (NP I, NP II, NP III and NP IV) are able to amplify antibody titers characteristic of both Th1 and Th2, but formulation NP III in particular is the most immunogenic.

On the other hand, if the titers of the mice of the NP III group are compared with those of the NP IV group, it can be observed that there is optimal cross-linking (Example 2, last paragraph), since although they have similar $IgG_1$ curves, the $IgG_{2a}$ titers for NP III are slightly greater than in the case of NP IV.

Regarding the results obtained in orally administered mice, it was observed that the only formulation that induced quantifiable levels of $IgG_1$ and $IgG_{2a}$ antibodies was NP III (FIG. 3).

After verifying that, under these experimental conditions, formulation NP III was the most effective, a similar study was performed modifying the administration dose of NP III. In this case the following formulations were administered (orally) to the animals:
a) Empty nanoparticles (NP)
b) 25 μg of encapsulated ovalbumin with nanoparticles cross-linked with 1,3-diaminopropane with encapsulated ovalbumin (NP III-25)
c) 50 μg of encapsulated ovalbumin with nanoparticles cross-linked with 1,3-diaminopropane with encapsulated ovalbumin (NP III-50)

Figure 4:
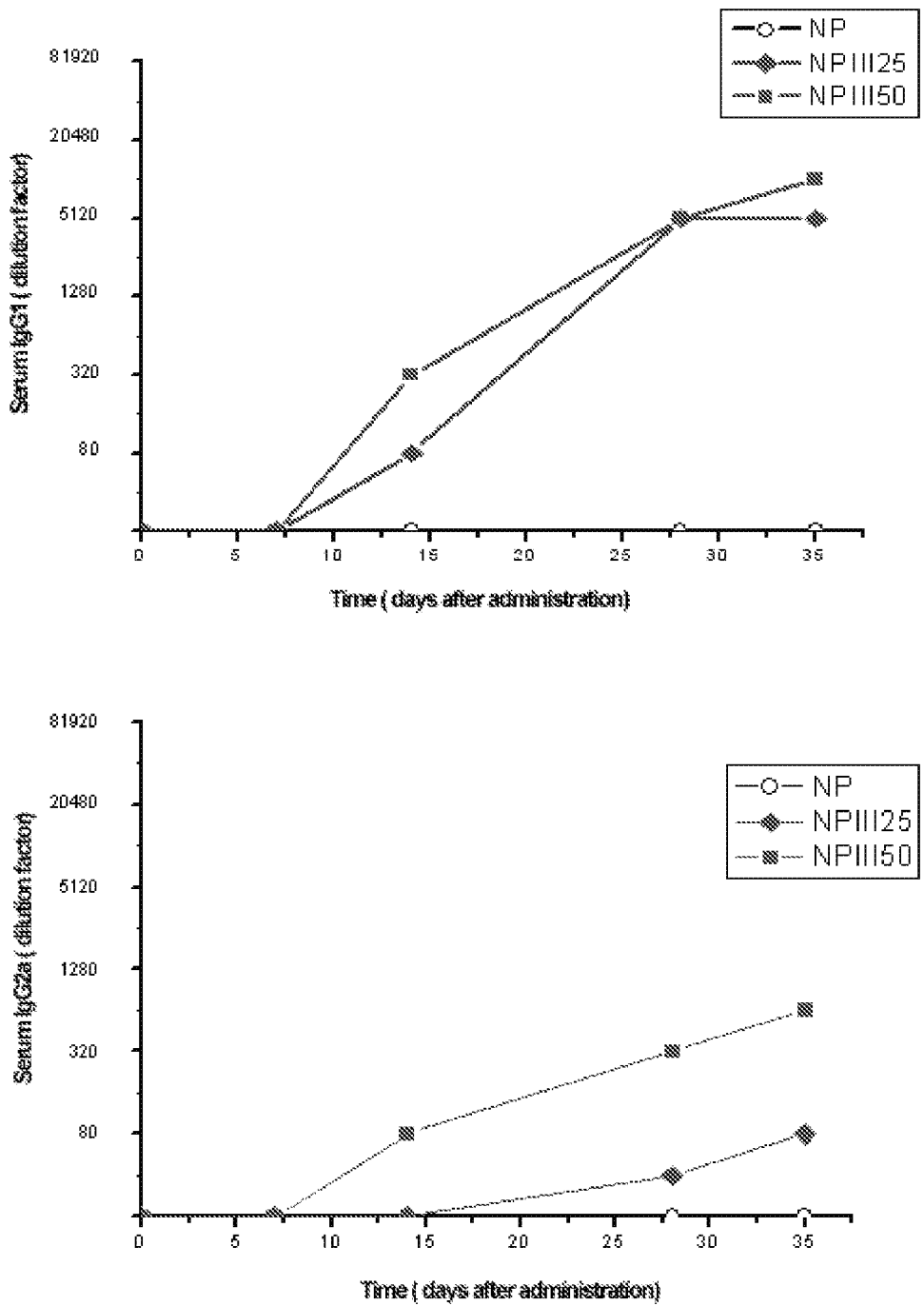
FIG. 4 shows a graph representing the levels of specific anti-ovalbumin antibodies ($IgG_1$, $IgG_{2a}$) after orally immunizing Balb/c mice with different encapsulated doses of ovalbumin (NP-III25 and NP-III50) and empty nanoparticles (NP) over time.

In this case, the results obtained (FIG. 4) show that anti-OVA $IgG_{2a}$ levels in serum were significantly greater when the dose was 50 μg.

Example 4

Quantification of Anti-OVA Antibody and Interleukin 10 (IL-10) Production after Administration of Ovalbumin Nanoparticles with *Brucella ovis* Lipopolysaccharide 40 BALB/c mice were immunized, divided into 8 groups according to the administration form. All the groups were administered the treatment intradermally (10 μg of ovalbumin). This time the different treatments were:
a) Ovalbumin (OVA) Solution
b) Ovalbumin absorbed onto alhydrogel (OVA-Alum)
c) Empty nanoparticles (NP)
d) Ovalbumin-coated nanoparticles (NP I)
e) Nanoparticles cross-linked with 1,3-diaminopropane with encapsulated ovalbumin (NP III)
f) Nanoparticles cross-linked with 1,3-diaminopropane with encapsulated ovalbumin and coated with *Brucella ovis* R-LPS(NP V)
g) Nanoparticles with encapsulated *Brucella ovis* R-LPS and coated with ovalbumin (NP VI)
h) Nanoparticles cross-linked with 1,3-diaminopropane with ovalbumin and encapsulated *Brucella ovis* R-LPS (NP VII)

The group that had been administered ovalbumin adsorbed onto alhydrogel intradermally (OVA-Alum) was taken as the positive control of the experiment.

Figure 5:
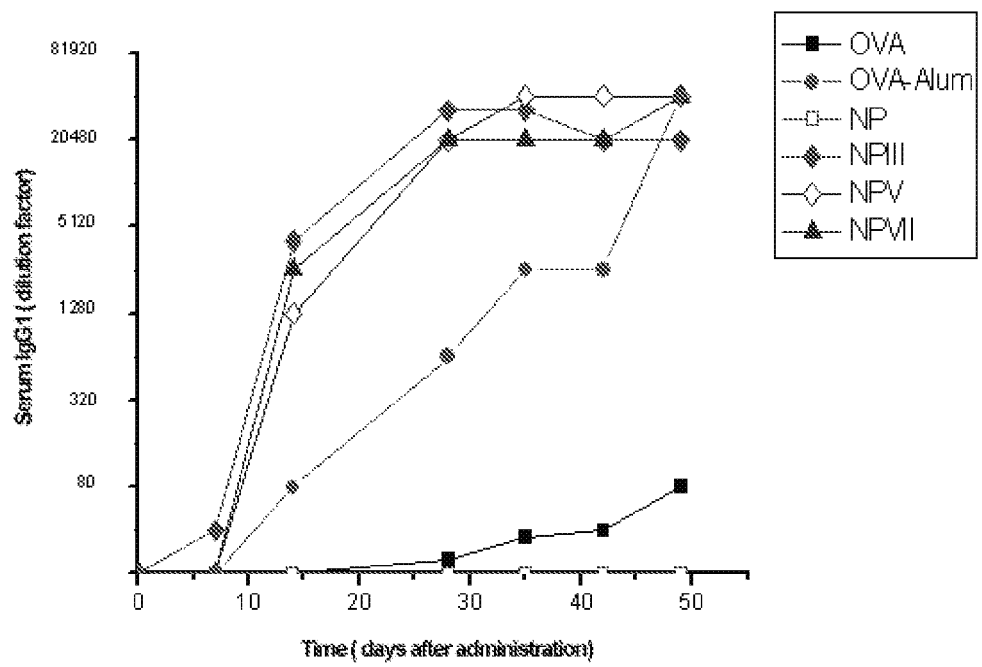
FIG. 5 shows a graph representing the levels of specific anti-ovalbumin antibodies ($IgG_1$) after intradermally immunizing Balb/c mice with an ovalbumin (OVA) solution, ovalbumin adsorbed in alhydrogel (OVA-Alum), and empty nanoparticles (NP), NP-I, NP-III, NP-V, NP-VI and NP-VII over time.
Figure 5:
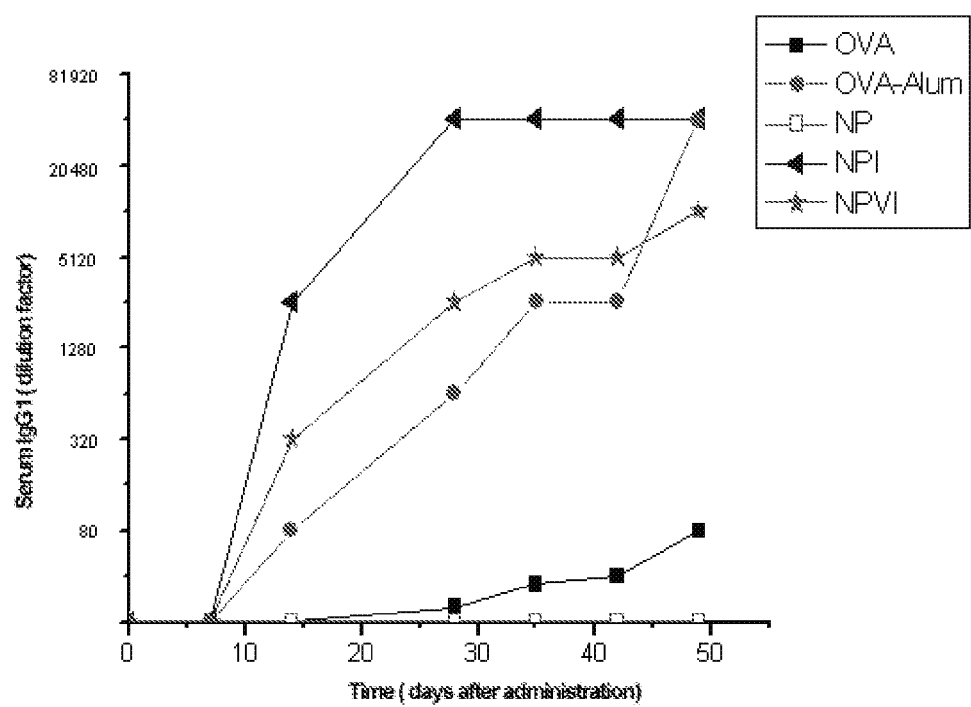

Successive blood extractions were performed on days 7, 14, 28, 35, 42 and 49 after immunization. The samples were processed (see Example 3) and the results were obtained and are included in FIGS. 5 and 6.

$IgG_1$ Response (FIG. 5): NP III, NP V and NP VII induced high $IgG_1$ levels in a much faster and more intense manner than the control formulation (OVA-Alum). Only 49 days after administration, the nanoparticle-based formulations and the control (OVA-Alum) show similar levels. Finally, R-LPS on the nanoparticle surface does not seem to have an effect on inducing $IgG_1$ levels.

On the other hand, NP I also shows a strong potential for inducing $IgG_1$ antibody production. Furthermore, as in the previous case, this phenomenon is faster and more intense than in the control formulation. When R-LPS is associated inside nanoparticles coated with OVA, a significant reduction in the serum $IgG_1$ titer with regard to NP I and control formulations is observed.

Figure 6:
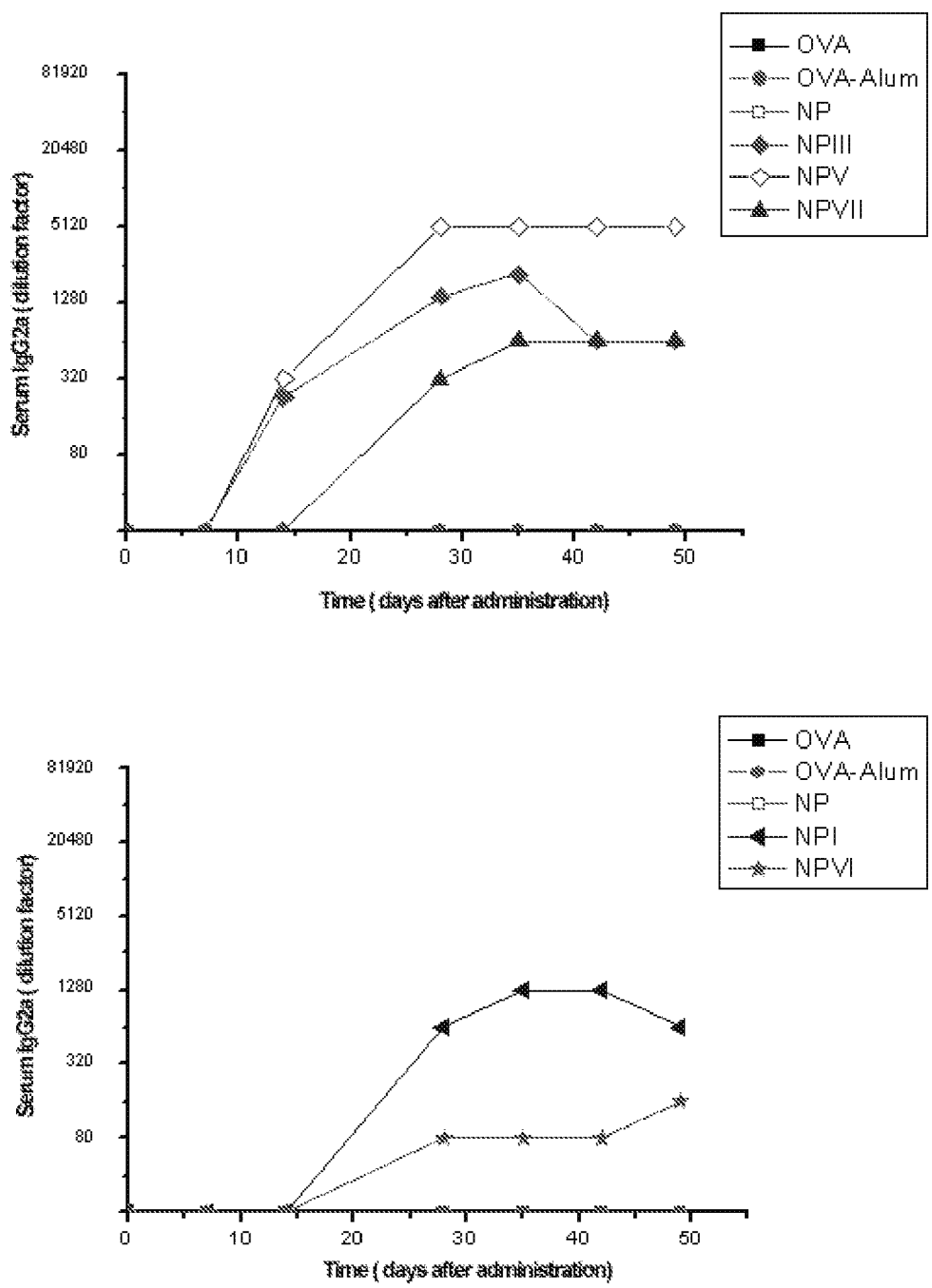
FIG. 6 shows a graph representing the levels of specific anti-ovalbumin antibodies ($IgG_{2a}$) after intradermally immunizing Balb/c mice with an ovalbumin (OVA)-free solution, ovalbumin adsorbed in alhydrogel (OVA-Alum), and empty nanoparticles (NP), NP-I, NP-III, NP-V, NP-VI and NP-VII over time.

$IgG_{2a}$ Response:

FIG. 6 shows the mouse serum $IgG_{2a}$ titers. In this case, none of the control formulations (OVA, NP, OVA-Alum) induces antibody titers. However, formulations with encapsulated OVA were able to provide high $IgG_{2a}$ titers, mainly when R-LPS was adsorbed on the outside of the nanoparticles (formulation NP V). On the other hand NP I appeared to be much more effective than NP VI for inducing a Th1 response measured in the serum $IgG_{2a}$ titer.

Figure 7:
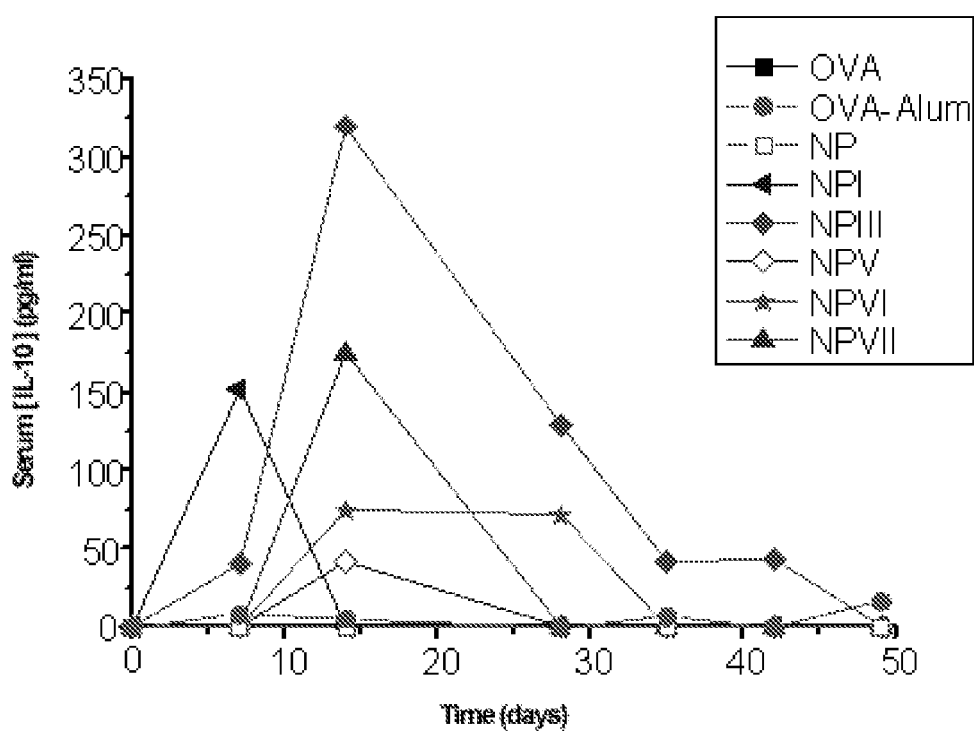
FIG. 7 shows a graph representing IL-10 serum concentration after intradermally immunizing Balb/c mice with ovalbumin (OVA)-free solution, ovalbumin adsorbed in alhydrogel (OVA-Alum), and empty nanoparticles (NP), NP-I, NP-III, NP-V, NP-VI and NP-VII over time.

IL-10:

FIG. 7 shows the serum IL-10 levels, which were determined by means of an ELISA kit (Biosource, Camarillo, USA). In this case, the controls were not able to induce serum IL-10 secretion either. However, all the nanoparticle formulations, to a greater or lesser degree, induced secretion of this cytokine. The formulation with ovalbumin adsorbed on the NP surface (NP I) allowed the induction of an IL-10 peak more quickly than the remaining formulations. However, the association of LPS (NP VI) significantly delayed (14 days) cytokine secretion. On the other hand, NP III was shown to be the most effective formulation for inducing serum IL-10, giving rise to levels that were two times higher than for NP I, although delayed over time by one week. The association of R-LPS in encapsulated nanoparticles OVA (NP V and NP VII) allowed the induction of more discrete IL-10 levels but with a maximum two weeks after administration. This potential of the formulations to induce significant IL-10 levels suggests their use as possible treatments for diseases characterized by imbalances in the Th1/Th2 balance due to the regulatory power of this cytokine [Zuany-Amorim et al, *J Clin Invest*, 95 (1995) 2644-2651; Stampfli et al, *Am J Respir Cell Mol Biol*, 21 (1999) 586-596; Hall et al, *Vaccine*, 21 (2003) 549-561].

Example 5

Preparation, Characterization and Administration of Nanoparticles with *Salmonella enteritidis* ChE Extract 5.1 Extraction of the *Salmonella enteritidis* ChE Extract The bacterial extract ChE (chaotropic extract) was obtained by following a protocol previously described by Altman et al. (Altman et al., Biochem J. (1982) 505-513). *Salmonella enteritidis* inoculums in their stationary stage were incubated in flasks containing 400 mL of BHI medium (Brain Heart Infusion, Difco Lab., Detroit, USA), at 37° C., 48 hours, without stirring. The cells were subsequently centrifuged (7,000×g, 30 minutes) and washed with PBS (Phosphate Buffered Saline; 10 mM; pH 7.4). The bacterial extract was obtained after treatment of the cellular pellet in 3M KSCN/PBS with magnetic stirring (1 h, room temperature), and subsequent centrifugation (35,000×g, 30 minutes). The supernatant, which contained the ChE extract, was collected and dialyzed first against PBS and then against deionized water. It was finally lyophilized and preserved at 4° C. until its later use.

5.2 Preparation of Nanoparticles with Ovalbumin and *Salmonella enteritidis* ChE (OVASAL)

100 mg of the methyl vinyl ether-maleic anhydride copolymer [Gantrez® AN 119] are dissolved in 3 mL of acetone, whereas on the other hand 5 mg of ovalbumin and 5 mg of the ChE extract are dispersed in 2 mL of acetone by ultrasonication (Microson™) for 1 minute with cooling. The ovalbumin and ChE dispersion is added to the polymer suspension and this is stirred for 30 minutes at room temperature. Subsequently, 10 mL of ethanol and 10 mL of deionized water are added to this phase under magnetic stirring. The resulting mixture is allowed to homogenize for 5 minutes. The nanoparticle suspension is then evaporated under reduced pressure until both organic solvents are removed and the final volume is adjusted with water to 10 mL. Then they are incubated with 0.1 mL of a 1% 1,3-diaminopropane solution.

The mixture is subjected to purification by ultracentrifugation (20 minutes at 27,000×g). The supernatants are removed and the residue is resuspended in a 5% sucrose aqueous solution. Finally, the resulting nanoparticle suspension is lyophilized.

5.3 Quantification of Anti-OVA Antibody Production after Immunization with OVASAL in BALB/c Mice 15 mice were intradermally immunized with 10 µg of ovalbumin and they were divided into 3 different groups according to the treatment received:
  a) Ovalbumin solution (OVA)
  b) Ovalbumin adsorbed onto alhydrogel (OVA-Alum)
  c) Ovalbumin nanoparticles and *Salmonella enteritidis* ChE (OVASAL)

Figure 8:
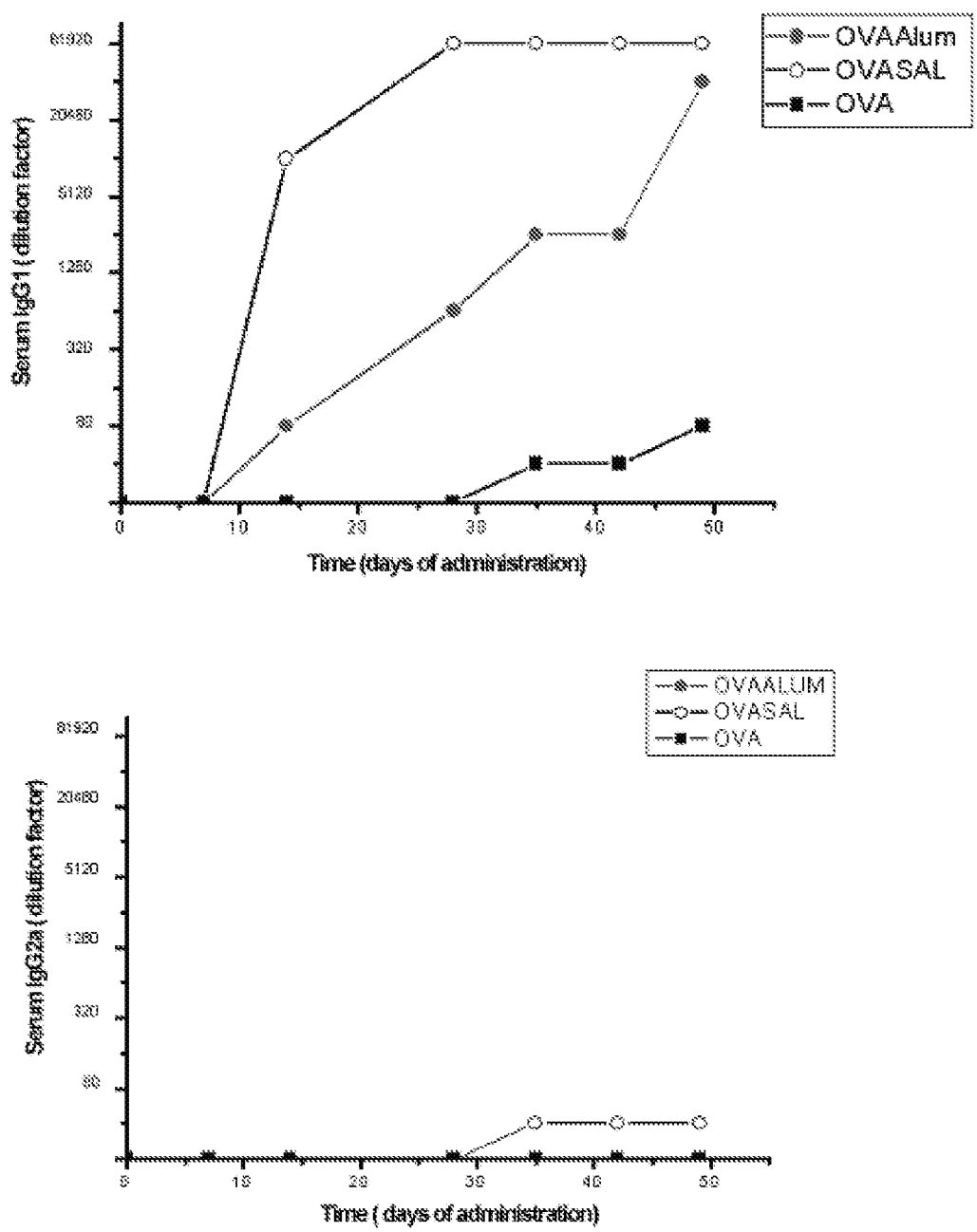
FIG. 8 shows a graph representing the levels of specific anti-ovalbumin antibodies ($IgG_1$, $IgG_{2a}$) after intradermally immunizing Balb/c mice with ovalbumin adsorbed in alhydrogel (OVA-Alum), OVASAL and ovalbumin (OVA) solution over time.

After the administration of the different formulations, blood was extracted from the retroorbital plexus on days 7, 14, 28, 35, 42 and 49, and the samples were processed as indicated in Example 3. The obtained results are shown in FIG. 8. Surprisingly, OVASAL considerably increased the $IgG_1$ titer, whereas the $IgG_{2a}$ titer remained at very low levels. This indicates that this formulation is able to enhance only the Th2 response, which was also much faster and more intense than it was for the control formulation (OVA-Alum). These results lead to thinking about the probable application as an adjuvant in vaccines where obtaining high antibody levels or against toxins secreted by microorganisms is of interest. It could also be applicable in certain autoimmune disease characterized by having a Th1 response that is excessively high in acute phases.

Example 6

Preparation and Characterization of Biodegradable Nanoparticles with the *Salmonella enteritidis* HE Extract (NP HE 3934)

6.1 Extraction and Characterization of the *Salmonella enteritidis* HE Antigen Complex 3934

The antigen used is a surface extract of *S. enteritidis* called HE (Hot Saline Extract) due to the fact that it releases the antigen complex in a saline medium and with heat. This HE contains phospholipids, surface proteins and smooth lipolysaccharide (S-LPS). The HE extract was obtained by a previously described method [Gamazo et al., Infect. Immun. (1989) 1419-1426]. After culturing the bacteria, *Salmonella enteritidis* 3934, in flasks containing Trypticase Soy Broth (TSB), the bacteria were centrifuged at 7,000×g for 30 minutes and were washed twice with saline solution. The live cells were resuspended in saline solution (10 g of wet cells in 100 mL) and is heated at 100° C. in flowing vapor for 15 minutes. After centrifugation (12,000×g, 10 minutes), the supernatant is dialyzed for 5 days against several changes with deionized water. The dialyzed material is ultracentrifuged for 4 hours at 60,000×g, and the pellet (HE) is resuspended in deionized water, lyophilized and stored at room temperature.

The characterization includes determining the protein and lipopolysaccharide percentage. Determination of the amount of proteins was carried out by the Lowry method. The *Salmonella enteritidis* antigen extract 3934 contains about 31% of proteins. The amount of LPS is indirectly determined by measuring one of its exclusive markers, KDO, by means of the thiobarbituric acid method. 0.86% of KDO, representing 65% of S-LPS, was obtained by means of this method.

6.2 Production and Physicochemical Characterization of the Nanoparticles with *Salmonella enteritidis* HE Extract 3934 (NP HE 3934)

First, 100 mg of the methyl vinyl ether-maleic anhydride copolymer are dissolved in 5 mL of acetone; antigen extract HE (4 mg), also resuspended in 1 mL of acetone, is added to this solution and it is mixed with magnetic stirring. This solution is allowed to incubate for 15 minutes at room temperature. 10 mL of ethanol and finally the same volume of water were subsequently added to this phase. The resulting mixture is allowed to homogenize for 5 minutes. The nanoparticle suspension is then evaporated under reduced pressure until both organic solvents are removed and the final volume is adjusted with water to 10 mL.

The suspension is subjected to purification by ultracentrifugation (10 minutes at 35,000×g). The supernatants are removed and the residue is resuspended in a 5% sucrose aqueous solution w/v. Finally, the resulting nanoparticle suspension is lyophilized, allowing it to maintain all its properties intact.

The formula resulting from the nanoparticle suspension prior to lyophilization is:

| | |
|---|---|
| Methyl vinyl ether-maleic anhydride copolymer (Gantrez ® AN-119) | 1.0% w/v |
| Antigen extract | 0.4% w/v |
| Sucrose | 5.0% w/v |
| Water f.i. | q.s. 10 mL |

[f.i.: for injection; q.s.: quantity sufficient for]

The size and surface charge of the nanoparticles is determined prior to the lyophilization process. The obtained nanoparticles have a mean size of less than 200 nm and a negative net surface charge (−20.1±3.2 mV). The production process yield was obtained by determining its weight after the lyophilization process. Starting from 100 mg of copolymer, the amount transformed into nanoparticle at the end of the process was determined and it was expressed as a percentage with respect to the initial copolymer mass.

The extract was quantified and detected by the bicinchoninic acid method. To that end, before adding the cross-linking agent, an aliquot (1 mL) of the nanoparticle suspension is taken. The nanoparticles are cleaved by adding 0.1 N NaOH, and this mixture is analyzed by the bicinchoninic acid colorimetric method for proteins prior to validation of the method. The validation was conducted with the extract dissolved in cleaved empty nanoparticles in 0.1 N NaOH. The bicinchoninic acid solution together with 5% cupric sulfate at a 100:2 ratio is added to the sample; the mixture is maintained at 37° C. for half an hour and is then spectrophotometrically measured at 562 nm.

The extract load is expressed as the amount of extract in μg per mg of nanoparticles and the encapsulation effectiveness is determined by relating the total encapsulated amount of extract with the initial amount.

Table 2 shows the antigen extract load in nanoparticles (μg of extract/mg nanoparticle) and encapsulation effectiveness (%).

TABLE 2

Physicochemical Characteristics of Gantrez ® AN 119 Nanoparticles Loaded with the Antigen Extract

| Formulation | Size (nm) | Encapsulated extract (μg/mg) | Encapsulation effectiveness$^a$ (%) |
|---|---|---|---|
| NP | 171.4 ± 3.9 | — | — |
| NP-HE S. enteritidis | 178 ± 55.4 | 18.1 ± 6.6 | 45.2 ± 5.4 |

$^a$The encapsulation effectiveness refers to the percent of encapsulated HE, and was calculated as the amount of antigen extract encapsulated times 100 and divided by the initial amount.

Figure 9:
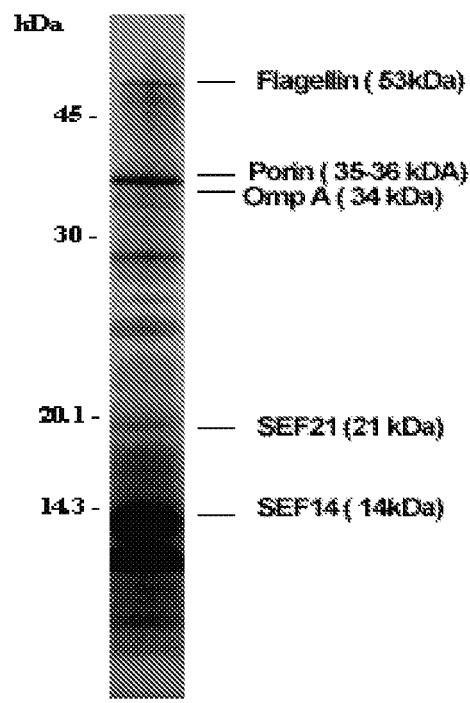
FIG. 9 shows the result of the separation of the HE extract by means of sodium dodecyl sulfate polyacrylamide gel electrophoresis (SDS-PAGE) and Coomassie staining for proteins (10 μg of extract per well).
Figure 10:
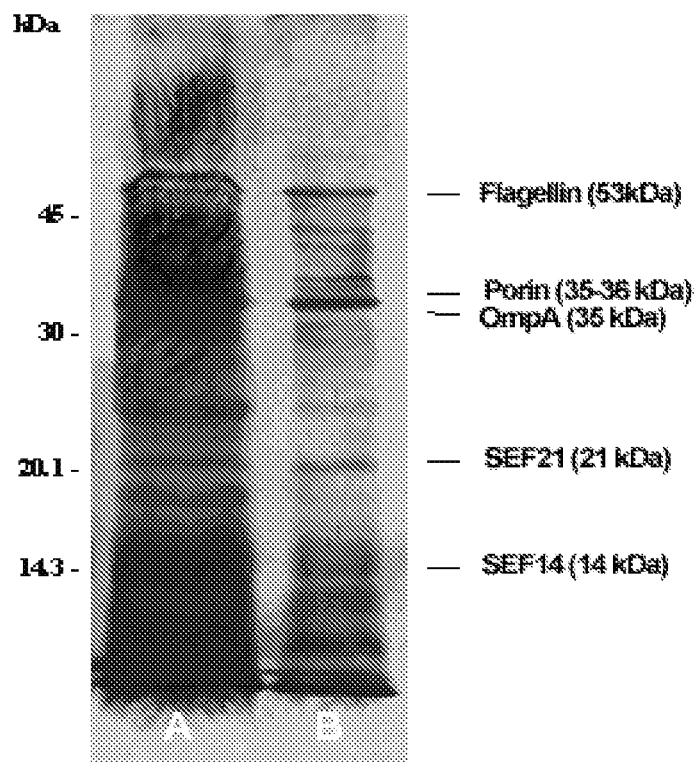
FIG. 10 shows the result of immunoblotting analysis of the HE extract before (A) and after (B) encapsulation, using a mixture of serums from infected hens.
Figure 11:
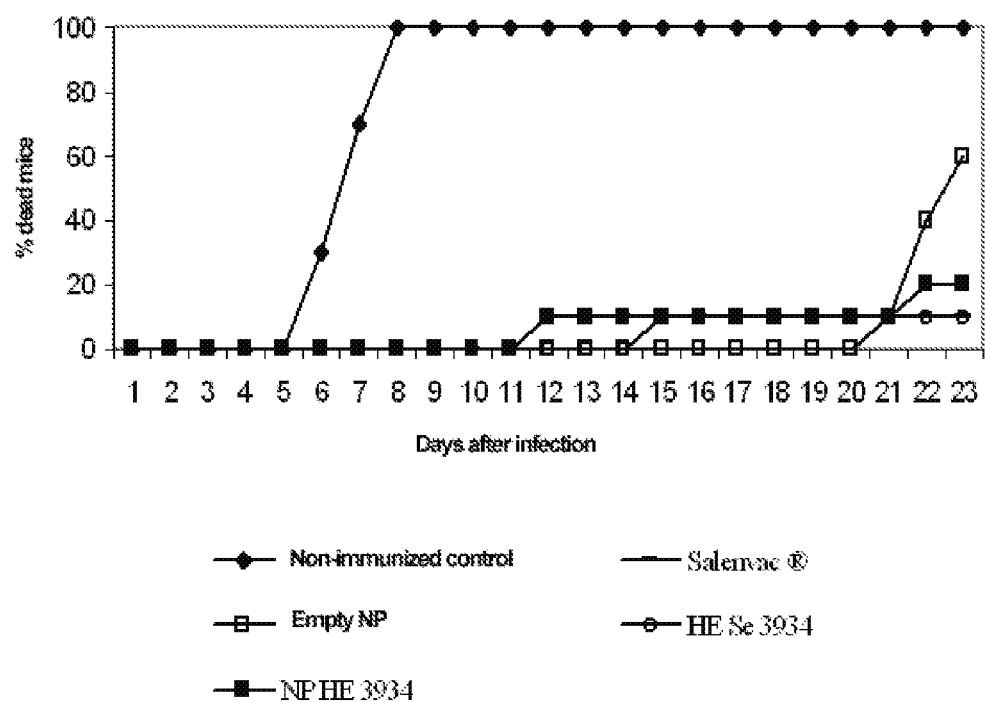
FIG. 11 is a graph illustrating the results of an intraperitoneal protection experiment in Balb/c mice with a lethal dose of $10^2$ colony forming units (CFU) of S. enteritidis 3934.

FIG. 9 reflects the of S. enteritidis HE protein standard, in which the different components can be distinguished: porins (about 36 kDa), OmpA (34 kDa) and the fimbriae SEF14 (14 kDa) and SEF21 (21 kDa). By means of a sodium dodecyl-sulfate polyacrylamide gel electrophoresis (SDS-PAGE) and immunoblotting it was confirmed that the encapsulated extract preserved its structural integrity and antigenicity. In FIG. 10 the antigenic profile of the extract before and after encapsulation can be observed.

Example 7

Study of the Protection Provided by the NP HE 3934 Vaccine Administered Intraperitoneally in Mice Nine-week old groups of BALB/c mice, each group consisting of 10 animals, were used. Vaccination was carried out with the nanoparticle vaccine preparation (NP HE 3934) described in Example 6 at a ratio of 30 μg of extract per animal, also including as controls: i) the same amount of the corresponding empty nanoparticles; ii) 30 μg/animal of the free, non-encapsulated HE extract, iii) 200 mL of the commercial vaccine Salenvac® (Intervet UK Limited, Walton, England); iv) saline solution.

Ten days after vaccination, they were intraperitoneally inoculated with a lethal dose of $10^2$ CFU of the S. enteritidis 3934 strain, and counts of the animals that died due to salmonellosis were performed after this inoculation. The results of the protection experiment demonstrate that the nanoparticle-based vaccine preparation (NP HE 3934) protected against S. enteritidis subcutaneously in a manner that is very similar to the commercial vaccine Salenvac®, as well as the HE antigen extract administered freely (HE Se 3934).

The results show that the encapsulation of HE extracts in nanoparticles does not increase protection levels in mice. On the other hand, mice immunization with empty nanoparticles induces a non-specific immune response which provides protection for three weeks. Nevertheless, it must be indicated that the administration route of the HE antigen, both in free and in encapsulated form, was intraperitoneal. Earlier studies suggest that oral or intranasal administration of the non-encapsulated antigens would cause their degradation before they reached the interaction sites with antigen-presenting cells.

Figure 12A:
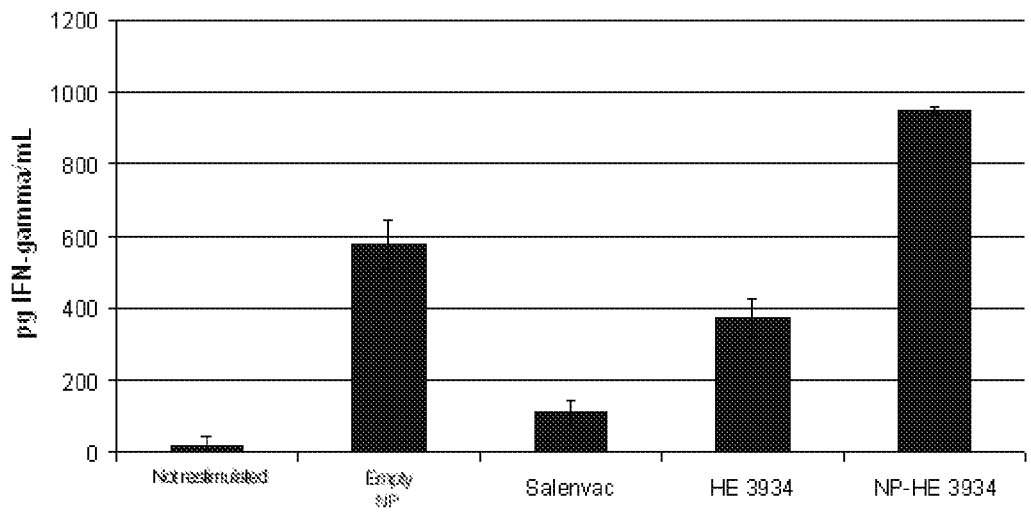
FIG. 12 shows a bar graph representing IFN-γ (A) and IL-4 (B) release by Balb/c mice spleen cells restimulated with HE extract.
Figure 12B:
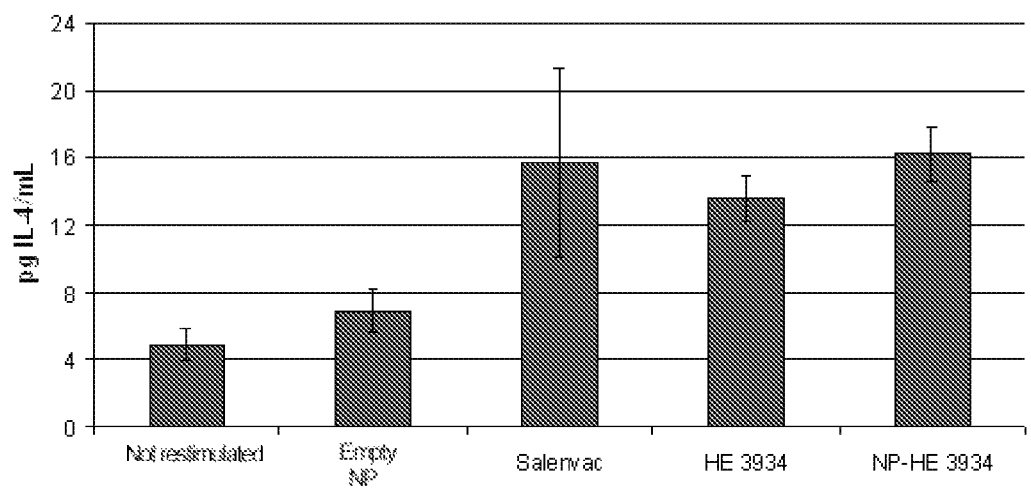

Furthermore, 10 days after vaccination, studies on the immunity provided by the nanoparticles were conducted in the moment of experimental infection, quantifying IFN-γ and IL-4 production levels (typical of Th1- and Th2-type immune responses, respectively) by spleen cells in the mice (FIG. 12). Blood $IgG_{2a}$ and $IgG_1$ antibody production (Th1 and Th2, respectively) was also determined (FIG. 13).

To study the Th1/Th2 immune balance induced by free and encapsulated HE extracts in the mice used in the study, IFN-γ and IL-4 levels produced by the spleen cells of the immunized animals were determined (FIG. 12). Panel A shows induced IFN-γ levels, indicating an increase of said production in the mice immunized with the nanoparticles (NP HE 3934). In contrast, panel B shows how there is no significant IL-4 production increase in mice immunized with the free HE extract (HE 3934) and mice immunized with the NP HE 3934 nanoparticles. In view of the obtained results, it can be affirmed that encapsulation of the HE extracts in nanoparticles favors an increase in the Th1-type response, reflected by an increase in IFN-γ production, compared to Th2.

Figure 13:
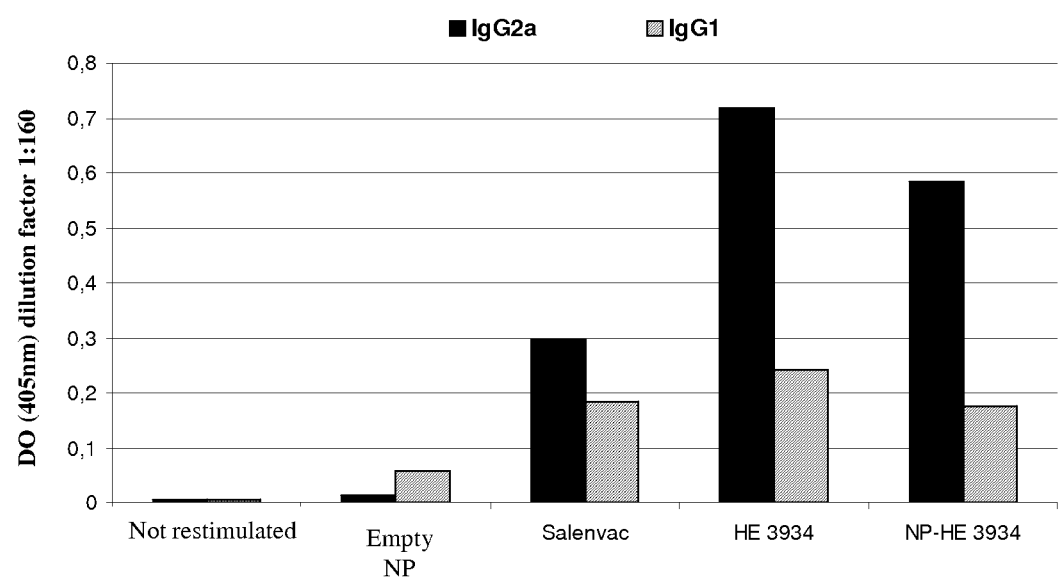
FIG. 13 shows a bar graph representing the result of an indirect ELISA on Balb/c mice serums compared to HE extract, using $IgG_1$ and $IgG_{2a}$ antibodies.

The production of antibodies specific against the S. enteritidis 3934 HE extracts in immunized mice was studied by means of indirect ELISA (FIG. 13). The non-immunized mice, or the mice immunized with empty nanoparticles (empty NP), did not produce $IgG_{2a}$ or $IgG_1$ antibodies against the S. enteritidis 3934 HE extract. Detected $IgG_{2a}$ levels were greater than those of $IgG_1$ in all mouse serums analyzed by ELISA. Nevertheless, an increase in the serological response in the mice immunized with encapsulated HE extracts (NP HE 3934) compared to the response shown by the mice immunized with free HE extracts (HE 3934) was not observed.

$IgG_{2a}$ is a dominant antibody isotype in Th1 immune responses, whereas $IgG_1$ has this same function for Th2 immune responses, which would confirm the results obtained in the IFN-γ and IL-4 release assay, indicating that intraperitoneal administration of nanoparticles with S. enteritidis HE extracts induces a predominant Th1-type immune response. This administration provides a degree of protection against salmonellosis that is similar to that observed when the free antigen is administered. Nevertheless, as previously discussed, the application of these non-encapsulated antigens through the mucosae would not give these levels of protection observed in this experiment due to the acid and enzymatic degradation they would experience on their passage through the animals' gastrointestinal tract.

The invention claimed is:

1. A method for stimulating a Th1 immune response against an allergen in a subject in need of treatment by immunotherapy against said allergen, said method comprising administering to the subject a Th1 immune response stimulating composition comprising nanoparticles based on a methyl vinyl ether and maleic anhydride (PVM/MA) copolymer, and an allergen, wherein said allergen is encapsulated inside said PVM/MA copolymer nanoparticles, wherein said allergen comprises an allergenic food or an allergenic food product extract, wherein the PVM/MA-based nanoparticles further comprise an immunostimulating agent at least partially coating the surface of said nanoparticles, and wherein the stimulation of the Th1 immune response in the subject is due to said nanoparticles based on a PVM/MA copolymer.

2. The method of claim 1, characterized by at least one of the following:
   (a) the nanoparticles further comprise a cross-linking agent;
   (b) the nanoparticles have a mean size that is equal to or less than 1.0 micrometer; and
   (c) the PVM/MA copolymer has a molecular weight comprised between 100 and 2,400 kDa.

3. The method according to claim 2, wherein the nanoparticles further comprise a cross-linking agent.

4. The method of claim 2, wherein the nanoparticles have a mean size that is between 10 and 900 nm.

5. The method of claim 2, wherein said PVM/MA copolymer has a molecular weight comprised between 200 and 2,000 kDa.

6. The method of claim 1, wherein said Th1 immune response stimulating composition is in a lyophilized form.

7. The method of claim 2, wherein said Th1 immune response stimulating composition is in a lyophilized form.

8. The method of claim 1, wherein said Th1 immune response stimulating composition is in an oral or parenteral administration form.

9. The method of claim 3, wherein said nanoparticle comprises:

| Component | % by weight with respect to total |
| --- | --- |
| PVM/MA | 84-99.998% |
| Cross-linking agent | 0.001-1% |
| Allergen | 0.001-15%. |

10. The method of claim 1, wherein said Th1 immune response stimulating composition comprising nanoparticles based on a PVM/MA copolymer is orally administered to said subject.

11. The method of claim 1, wherein said allergen comprises an allergenic food.

12. The method of claim 1, wherein said allergen comprises an allergenic food product extract.

* * * * *

UNITED STATES PATENT AND TRADEMARK OFFICE
CERTIFICATE OF CORRECTION

PATENT NO. : 8,895,067 B2  
APPLICATION NO. : 11/568455  
DATED : November 25, 2014  
INVENTOR(S) : Irache Garreta et al.

Page 1 of 1

It is certified that error appears in the above-identified patent and that said Letters Patent is hereby corrected as shown below:

On the title page item [56],

Foreign Patent Documents: "ES 2098189" should read -- ES 2098188 --.

Foreign Patent Documents: "WO 0620698" should read -- WO 9620698 --.

Signed and Sealed this
Twenty-eighth Day of April, 2015

Michelle K. Lee
*Director of the United States Patent and Trademark Office*